US010456359B2

(12) United States Patent
Chigurupati et al.

(10) Patent No.: US 10,456,359 B2
(45) Date of Patent: *Oct. 29, 2019

(54) SYNERGISTIC BEVERAGE COMPOSITION

(71) Applicant: Harsha Chigurupati, Hyderabad (IN)

(72) Inventors: Harsha Chigurupati, Hyderabad (IN); Manish Radheshyam Biyani, Hyderabad (IN); Biswajit Auddy, Hyderabad (IN); Shrabana Chakrabarti, Hyderabad (IN)

(73) Assignee: Harsha Chigurupati, Hyderabad (IN)

(*) Notice: Subject to any disclaimer, the term of this patent is extended or adjusted under 35 U.S.C. 154(b) by 140 days.

This patent is subject to a terminal disclaimer.

(21) Appl. No.: 15/186,977

(22) Filed: Jun. 20, 2016

(65) Prior Publication Data
US 2016/0367478 A1 Dec. 22, 2016

(30) Foreign Application Priority Data
Jun. 19, 2015 (IN) .......................... 3070/CHE/2015

(51) Int. Cl.
| A61K 9/00 | (2006.01) |
| A61K 38/05 | (2006.01) |
| A61K 31/047 | (2006.01) |
| A61K 47/12 | (2006.01) |
| A61K 31/704 | (2006.01) |
| A23L 2/52 | (2006.01) |
| A23L 33/10 | (2016.01) |
| A23L 33/105 | (2016.01) |
| A23L 33/18 | (2016.01) |
| A61K 38/01 | (2006.01) |

(52) U.S. Cl.
CPC .............. *A61K 9/0095* (2013.01); *A23L 2/52* (2013.01); *A23L 33/10* (2016.08); *A23L 33/105* (2016.08); *A23L 33/18* (2016.08); *A61K 31/047* (2013.01); *A61K 31/704* (2013.01); *A61K 38/018* (2013.01); *A61K 38/05* (2013.01); *A61K 47/12* (2013.01); *A23V 2002/00* (2013.01)

(58) Field of Classification Search
CPC ...... A61K 9/0095; A61K 2/52; A61K 31/047; A61K 31/746; A61K 38/018; A61K 38/05; A61K 47/12; A61K 33/10; A61K 33/18; A61K 33/105; A23V 2002/00
USPC .......................................................... 514/33
See application file for complete search history.

(56) References Cited

U.S. PATENT DOCUMENTS

| 3,107,605 A * | 10/1963 | Aldrich ................. C13B 10/04 100/75 |
| 4,596,825 A | 6/1986 | Suda et al. |
| 4,987,123 A | 1/1991 | Masaki et al. |
| 6,099,844 A * | 8/2000 | Rohde, Jr. .......... C12Y 302/0100 424/727 |
| 6,287,757 B1 | 9/2001 | Abe et al. |
| 6,713,091 B1 | 3/2004 | Kim |
| 9,149,491 B2 * | 10/2015 | Chigurupati ....... A61K 31/7016 |
| 2005/0079590 A1 * | 4/2005 | Saha .................... C12P 7/18 435/158 |
| 2009/0162483 A1 * | 6/2009 | Constantine ............. A23L 2/52 426/62 |
| 2010/0037353 A1 | 2/2010 | Suzuki et al. |
| 2010/0086666 A1 | 4/2010 | Adelman |
| 2010/0234308 A1 | 9/2010 | Komatsu et al. |

FOREIGN PATENT DOCUMENTS

| CN | 1586489 A | 3/2005 |
| CN | 1706394 A | 12/2005 |
| CN | 1709272 A | 12/2005 |
| CN | 1736270 A | 2/2006 |
| CN | 101332289 A | 12/2008 |
| CN | 101633683 A | 1/2010 |
| CN | 101669962 A | 3/2010 |
| CN | 1985987 B | 5/2010 |
| CN | 102302502 A | 1/2012 |
| CN | 103404934 A | 11/2013 |
| CN | 103445175 A | 12/2013 |
| CN | 103622981 A | 3/2014 |
| EP | 0336960 A1 | 10/1989 |
| EP | 0502554 A2 | 9/1992 |
| JP | 6336773 A | 2/1988 |

(Continued)

OTHER PUBLICATIONS

Kalac, J. of the Sci. Food and Agric., 2013, 93, 209-218; published online Nov. 21, 2012.*
Putet et al, Pediatric Research, 1987, 21, 458-461.*
Remington, The Science and Practice of Pharmacy, 20th Ed., 2000, pp. 734, 1016, 1232.*
Li et al, International Journal of Molecular Science, 2011, 12, 905-916.*
Afford et al., "Distinct Patterns of Chemokine Expression Are Associated With Leukocyte Recruitment in Alcoholic Hepatitis and Alcoholic Cirrhosis"; Journal of Pathology; 1998; pp. 82-89; vol. 186.
Albano, "Alcohol, oxidative stress and free radical damage"; Proceedings of the Nutrition Society; 2006; pp. 278-290; vol. 65.

(Continued)

*Primary Examiner* — Ganapathy Krishnan
(74) *Attorney, Agent, or Firm* — Campbell Stephenson LLP; Shiv S. Naimpally

(57) ABSTRACT

Disclosed is a synergistic beverage composition for alleviating alcohol-induced oxidative stress, hepatic stress, CNS stress, veisalgia and modulating immunology parameters. The composition includes saponin glycoside, amino acid derivative and sugar or sugar alcohol as active ingredients and pH adjusting agents and flavoring agents as inactive ingredients. The calculated proportions of amino acid derivatives, Saponin glycoside and sugar or sugar alcohol in the alcohol exhibit synergistic effects, thereby alleviating oxidative stress, hepatic stress, CNS stress, veisalgia and modulating immunology parameters, which could ultimately leads to prevention of alcohol-induced damage or impairment of organs, which could be temporary or permanent.

18 Claims, No Drawings

(56) References Cited

FOREIGN PATENT DOCUMENTS

| JP | 614746 A | 1/1994 |
|---|---|---|
| JP | 200072669 A | 3/2000 |
| JP | 2008266203 A | 11/2008 |
| WO | 8904165 A1 | 5/1989 |
| WO | 0217939 A1 | 3/2002 |
| WO | 2014177989 A2 | 11/2014 |

OTHER PUBLICATIONS

Altura et al., "Association of Alcohol in Brain Injury, Headaches, and Stroke with Brain-Tissue and Serum Levels of Ionized Magnesium: A Review of Recent Findings and Mechanisms of Action"; Alcohol; 1999; pp. 119-130; vol. 19:2.
Ellman et al., "A New and Rapid Colorimetric Determination of Acetylcholinesterase Activity"; Biochemical Pharmacology; 1961; pp. 88-95; vol. 7.
Elmore, "Apoptosis: A Review of Programmed Cell Death"; Toxicologic Pathology; 2007; pp. 495-516; vol. 35.
Gao et al., "Liver: An Organ with Predominant Innate Immunity"; Hepatology; 2008; pp. 729-736; vol. 47.
Ge et al., "High Mobility Group Box-1 (HMGB1) Participates in the Pathogenesis of Alcoholic Liver Disease (ALD)"; The Journal of Biological Chemistry; 2014; pp. 22672-22691; vol. 289:33.
Hawkins et al., "The Metabolism of Ethanol and Its Metabolic Effects"; Pharmacological Reviews; 1972; pp. 67-157; vol. 24:1.
He et al., "Increased MCP-1 and Microglia in Various Regions of the Human Alcoholic Brain"; 2008; Exp Neurol.; pp. 349-358; vol. 210:2.
Holloway et al., "Delayed Ethanol Effects on Physiological and Behavioral Indices in the Rat"; Alcohol; 1993; pp. 511-519; vol. 10.
Karadayian et al., "Alcohol hangover: Type and time-extension of motor function impairments"; Behavioural Brain Research; 2013; pp. 165-173; vol. 247.
Ki et al., "Interleukin-22 treatment ameliorates alcoholic liver injury in a murine model of chronic-binge ethanol feeding: Role of STAT3"; Hepatology; 2010; pp. 1291-1300; vol. 52:4.
Kim et al., "The Effects of Alcohol Hangover on Cognitive Functions in Healthy Subjects"; Intern. J. Neuroscience; 2003; pp. 581-594; vol. 113.
Kim et al., "Effects of alcohol hangover on cytokine production in healthy subjects"; Alcohol; 2003; pp. 167-170; vol. 31.
Koop, "Alcohol Metabolism's Damaging Effects on the Cell: A Focus on Reactive Oxygen Generation by the Enzyme Cytochrome P450 2E1"; Alcohol Research & Health; 2006; pp. 274-280; vol. 29:4.
Lemmers et al., "The Interleukin-17 Pathway Is Involved in Human Alcoholic Liver Disease"; Hepatology; 2009; pp. 646-657; vol. 49.
Liangpunsakul et al., "Activity of CYP2E1 and CYP3A Enzymes in Adults With Moderate Alcohol Consumption: A Comparison With Nonalcoholics"; Hepatology; 2005; pp. 1144-1150; vol. 41.
Marsillach et al., "The role of circulating monocyte chemoattractant protein-1 as a marker of hepatic inflammation in patients with chronic liver disease"; Clinical Biochemistry; 2005; pp. 1138-1140; vol. 38.
Maxwell et al., "Acetate Causes Alcohol Hangover Headache in Rats"; PLoS One; 2010; pp. 1-9; vol. 5:12.
McKinney et al., "Alcohol Hangover Effects on Measures of Affect the Morning After a Normal Nights Drinking"; Alcohol & Alcoholism; 2006; pp. 54-60; vol. 41:1.
Morris, "Developments of a water-maze procedure for studying spatial learning in the rat"; Journal of Neuroscience Methods; 1984; pp. 47-60; vol. 11.
Nuutinen et al., "Elevated Blood Acetate as Indicator of Fast Ethanol Elimination in Chronic Alcoholics"; Alcohol; 1985; pp. 623-626; vol. 2.
Padilla et al., "Rat C-reactive protein activates the autologous complement system"; Immunology; 2003; pp. 564-571; vol. 109.
Pattichis et al., "5-Hydroxytryptamine release from platelets by different red wines: implications for migraine"; European Journal of Pharmacology; 1995; pp. 173-177; vol. 292.
Prat et al., "Neurocognitive effects of alcohol hangover"; Addictive Behaviors; 2008; pp. 15-23; vol. 33.
Qin et al., "Chronic ethanol increases systemic TLR3 agonist-induced neuroinflammation and neurodegeneration"; Journal of Neuroinflammation; 2012; pp. 1-18; vol. 9:130.
Reichenberg et al., "Cytokine-Associated Emotional and Cognitive Disturbances in Humans"; Arch Gen Psychiatry; 2001; pp. 445-452; vol. 58.
Rico et al., "Ethanol alters acetylcholinesterase activity and gene expression in zebrafish brain"; Toxicology Letters; 2007; pp. 25-30; vol. 174.
Ronis et al., "The Role of Ethanol Metabolism in Development of Alcoholic Steatohepatitis in the Rat"; Alcohol; 2010; pp. 157-169; vol. 44:2.
Sozio et al., "Alcohol and lipid metabolism"; Am J Physiol Endocrinol Metab; 2008; pp. E10-E16; vol. 295.
Sullivan et al., "Neurocircuitry in alcoholism: a substrate of disruption and repair"; Psychopharmacology; 2005; pp. 583-594; vol. 180.
Szabo et al., "Focus on: Alcohol and the Liver"; Alcohol and Health; 2010; pp. 87-96; vol. 33:1.
Tiwari et al., "Suppression of neuro-inflammatory signaling cascade by tocotrienol can prevent chronic alcohol-induced cognitive dysfunction in rats"; Behavioural Brain Research; 2009; pp. 296-303; vol. 203.
Verster et al., "Alcohol Hangover Effects on Memory Functioning and Vigilance Performance after an Evening of Binge Drinking"; Neuropsychopharmacology; 2003; pp. 740-746; vol. 28.
Vorhees et al., "Morris water maze: procedures for assessing spatial and related forms of learning and memory"; Nature Protocols; 2006; pp. 848-858; vol. 1:2.
Wang et al., "Regional cell shape changes control form and function of Kupffer's vesicle in the zebrafish embryo"; Dev Biol.; 2012; pp. 52-62; vol. 370:1.
Wang et al., "Ischemic cerebral tissue and MCP-1 enhance rat bone marrow stromal cell migration in interface vulture"; Experimental Hematology; 2002; pp. 831-836; vol. 30.
Wheeler et al., "The Role of Kupffer Cell Oxidant Production in Early Ethanol-Induced Liver Disease"; Free Radical Biology & Medicine; 2001; pp. 1544-1549; vol. 31:12.
Worek et al., "Determination of acetylcholinesterase activity by the Ellman assay: A versatile tool for in vitro research on medical countermeasures against organophosphate poisoning"; Drug Test. Analysis; 2012; pp. 282-291; vol. 4.
Yamada et al., "High Mobility Group Protein 1 (HMGB1) Quantified by ELISA with a Monoclonal Antibody That Does Not Cross-React with HMGB2"; Clinical Chemistry; 2003; pp. 1535-1537; vol. 49.9.
Zakhari., "Overview: How Is Alcohol Metabolized by the Body?"; Alcohol Research & Health; 2006; pp. 245-254; vol. 29:4.
Zhang et al., "RIP3, an Energy Metabolism Regulator That Switches TNF-Induced Cell Death from Apoptosis to Necrosis"; Science; 2009; pp. 332-336; vol. 325.
Zou et al., "Release of Neuronal HMGB1 by Ethanol through Decreased HDAC Activity Activates Brain Neuroimmune Signaling"; PLOS ONE; 2014 pp. 1-12; vol. 9:2.

* cited by examiner

SYNERGISTIC BEVERAGE COMPOSITION

CROSS REFERENCE TO RELATED APPLICATION

This application claims priority to Indian Patent Application No. 3070/CHE/2015 filed Jun. 19, 2015, the disclosure of which is hereby incorporated in its entirety by reference.

FIELD OF THE INVENTION

The invention relates to a synergistic beverage composition for alleviating alcohol-induced oxidative stress, hepatic stress, CNS stress, veisalgia and modulating immunology parameters. The invention also relates to a method for preparation of such composition.

BACKGROUND OF THE INVENTION

In 2010, the World Health Organization ("WHO") reported that 10% of the adult population in the United States suffered from alcohol use disorders ("AUD"). AUDs have a debilitating effect and are known to lead to 60 medical conditions affecting the immune system, central nervous system (CNS), liver, etc. (Alcohol Research & Health, 2011, 34, 2).

The acute, as well as chronic, toxic effects of ethanol may include irreversible organ damage. Disorders relating to memory loss, veisalgia, CNS and hepatoxicity have been well established. Also, studies have been made and theories have been postulated that cite ethanol as a cause for physiological disorders.

The invention focusses on certain pathways to reduce overall toxic effect of alcohol including effects on the brain, the liver, immunology, blood plasma and alcohol-induced veisalgia. Alcohol-induced veisalgia is the adverse effects experienced in the morning after a binge drinking episode. When the symptoms of veisalgia are initiated, blood alcohol level is usually zero or close to zero. Veisalgia is characterized by a variety of symptoms including dry mouth, nausea, sleepiness, headache, light-headedness, lack of concentration, etc. Veisalgia does not have a single cause; multiple physiological, metabolic, neuro-pharmacological and neuro-immunological effects, which are triggered by binge alcohol consumption that eventually leads to the Veisalgia syndrome. Acetate could be a primary contributor to the headache component of the Veisalgia, while acetaldehyde may also cause Veisalgia symptoms in humans.

Among the symptoms of veisalgia are memory decrements (Verster et al. "Alcohol Hangover Effects on Memory Functioning and Vigilance Performance after an Evening of Binge Drinking." Neuropsychopharmacology, 28, 2003, 740-746; McKinney and Coyle, "Alcohol Hangover Effects on Measures of Affect the Morning after a Normal Night's Drinking." Alcohol and Alcoholism Vol. 41, No. 1, pp. 54-60, 2006). Further, it has been shown that, during veisalgia, a patient's ability to perform complex tasks is compromised, which indicates a diminishment of the patient's memory function (Kim et al. "The Effects of Alcohol Hangover on Cognitive Functions in Healthy Subjects."International Journal of Neuroscience, 113, 2003, 581-594). Moreover, acute, as well as chronic, administration of alcohol can modulate cognition and lead to several neurocognitive effects, namely, impairment in intellectual ability, all modes of learning procedure, planning capacity, visuomotor coordination, memory, etc (Sullivan and Pfefferbaum. "Neurocircuitry in Alcoholism: A Substrate of Disruption and Repair." Psychopharmacology, 180, 2005, 583-594).

The role of inflammatory neurodegeneration in alcohol-related neuropathology of humans suggests that the enhanced expression of Monocyte Chemoattractant Protein-1 (MCP-1) and microglia activities in alcoholic brains could contribute to ethanol-induced pathogenesis. (Jun He, Fulton T. Crews. "Increased MCP-1 and Microglia in Various Regions of the Human Alcoholic Brain." Experimental Neurology, 210, 2, 2008, 349-358).

Alcohol Veisalgia and Immunology Factors

Crews et al. have shown glycyrrhizin inhibits High-mobility group protein B1 (HMGB1) and also acts as an Toll-like receptor 4 (TLR4) antagonist as well as inhibitor of microglial activation, all blocked ethanol-induced expression of pro-inflammatory cytokines like TNF-$\alpha$ and IL-1b.

HMGB1 is a highly conserved eukaryotic non-histone chromosomal protein. Upon stimulation, HMGB1 undergoes translocation from the nucleus to the cytoplasm, and it is then secreted via the lysosomal pathway in most cells by exosomes in enterocytes or by the inflammasome in immune cells. HMGB1 can trigger an inflammatory response, when passively released from injured or necrotic cells due to loss of membrane integrity or when secreted by activated monocytes and macrophages as a delayed response to lipopolysaccharide. HMGB1 expression, translocation and secretion progressively increase, both in liver and serum, during alcoholic liver diseases (Xiaodong Ge, et al 2014 Journal of biological chem., 289, 33, 22672-22691).

These results support the hypothesis that ethanol alters histone deacetylase (HDACs) that regulates HMGB1 release and that danger signal HMGB1 as endogenous ligand for TLR4 mediates ethanol-induced brain neuro-immune signalling through activation of microglial TLR4. These findings provide new therapeutic targets for brain neuro-immune activation and alcoholism (Zou J Y, Crews F T. "Release of Neuronal HMBG1 by Ethanol Through Decreased HDAC Activity Activates Brain NeuroimmuneSignaling." PLoSONE, 9, 2, 2014, e87915.

Among the hangover veisalgia symptoms, incidence of headaches is most common. Headaches may be explained not only by the vasodilatation effects of alcohol but also by increases in serotonin, histamine, and prostaglandin levels (Pattichis et al., Eur J Pharmacol, 292, 1995, 173-177) or by a profound deficit in ionized $Mg^{++}$, which may be reversed by the administration of $MgSO_4$ (Altura and Altura, 1999, Alcohol, Vol. 19, No. 2, pp. 119-130). Recent findings suggest that higher levels of cytokines could also lead to a hangover veisalgia headache. Some researchers also demonstrated that acetate could also contribute to the hangover veisalgia headache by increasing adenosine in the brain tissues (Christina R. Maxwell, et al, Acetate causes alcohol hangover headache in rats, Plos one, 5, 12, 2010, 01-09). Apart from these, acetaldehyde and congener content contribute a small but significant additional effect.

Further, physiological changes during a state of veisalgia, in particular, nausea, headache, and fatigue have been suggested to be mediated by changes in immune system function. The state of veisalgia has been defined as being initiated 13 hours after drinking 1.5 g/kg of alcohol (blood alcohol level). The values of the cytokines like Interleukin (IL), IL-10, IL-12 and IFN-$\alpha$ shows significant increase 13 hours after alcohol consumption. An increase in production of IL-10, as a response to pro-inflammatory cytokine production, thus supports the suggestion of impaired cellular immunity during Veisalgia (Kim et al. "Effects of Alcohol Hangover on Cytokine Production in Healthy Subjects." Alcohol, 31, 3, 2003, 167-170).

Oxidative Stress and Liver

There are three principal reaction mechanisms capable of oxidizing ethanol to acetaldehyde. These are the alcohol dehydrogenase (ADH), catalase and microsomal ethanol oxidizing systems (MEOS). Acute studies involving a single dose of ethanol primarily metabolized through alcohol dehydrogenase system without significant involvement of catalase. However, chronic exposure of ethanol may involve catalase pathway, as a minor pathway, as demonstrated by the large amounts of catalase found in various tissues and the presence of various peroxide-generating systems. MEOS is a mixed function oxidase system in mammalian liver microsomes, which plays a major role in hepatic metabolism of many drugs including ethanol to acetaldehyde by nicotinamide adenine dinucleotide phosphate-oxidase (NADPH) and oxygen-dependent oxidation by cytochrome P-450s (Hawkins R D, Kalant H. "The Metabolism of Ethanol and its Metabolic Effects." Pharmacological Review 24, 1 1972, 67-157). Further, cytochrome P450 (CYP) 2E1-dependent microsomal monoxygenase system, the mitochondrial respiratory chain and the cytosolic enzymes xanthine oxidase and the aldehyde oxidases have been implicated as sources of $O_2$ and $H_2O_2$ in parenchymal cells during ethanol intoxication (Albano E. "Alcohol, Oxidative Stress, and Free Radical Damage. Proceedings of the Nutrition Society, 65, 03, 2006, 278-290). CYP2E1-dependent monoxygenase activity increases by 10-20fold in chronic alcoholism (Liangpunsakul et al. "Activity of CYP2E1 and CYP3A Enzymes in Adults with Moderate Alcohol Consumption: A Comparison With Nonalcoholics." Hepatology, 41, 5, 1144-50). In liver, the CYP2E1 content is positively correlated with NADPH oxidase activity and lipid peroxidation (Ronis et al., "The Role of Ethanol Metabolism in Development of Alcoholic Steatohepatitis in the Rat", Alcohol. 44, 2, 2010, 157-169.). Thus, one of the major sources of reactive oxygen species ("ROS") of ethanol-induced oxidative stress is the alcohol-inducible cytochrome P450 (CYP) 2E. The other main contributing factors that produce ROS are the mitochondrial electron transport chain reactions, activated phagocytes and impairment of endogenous antioxidant defences.

The primary pathway of alcohol metabolism, when alcohol is consumed below moderate amounts, is catalysis in the cytoplasm of hepatocytes by alcohol dehydrogenase (ADH) to form acetaldehyde. The accumulation of NADH in the liver seems to be critical in liver damage in chronic alcohol use. Acetaldehyde produced through microsomal ethanol oxidation system (MEOS) accounts for less than 10% of the liver capacity to oxidize ethanol. At higher alcohol levels (>100 mg/dl), MEOS involves CYP450 (2E1, 1A2 & '3A4), which plays a pivotal role in alcohol metabolism using NADPH as a cofactor and $O_2$. (Koop, D. R., "Alcohol Metabolism's Damaging Effects on the Cell.", Alcohol Research & Health, 29, 4, 2006, 274-280). Acetaldehyde is oxidized to acetate in the liver via mitochondrial nicotinamide adenine dinucleotide ($NAD^+$) dependent aldehyde dehydrogenase (ALDH). ADH activity is 3 times more than ALDH, and so accumulation of Acetaldehyde takes place. Acetate is further metabolized to acetyl CoA and can enter the TCA cycle or synthesis of fatty acids. Each of these pathways results in the formation of free radicals (such as ROS) with concomitant changes in the cell's redox state (i.e., nicotinamide adenine dinucleotide ("$NAD^+$") reduced by two electrons). (Wheeler M D. et al. "The Role of Kupffer Cell Oxidant Production in Early Ethanol-Induced Liver Disease." Free Radical Biology & Medicine, 31, 12, 2001, 1544-1549). The redox state in relation to alcohol metabolism causes inhibition of $NAD^+$-mediated enzyme reactions typical to the normal metabolism of the hepatocyte, leading to positive $NADH/NAD^+$ ratio, which causes alcohol-induced fatty liver production, which leads to oxidative stress through a variety of pathways mentioned above. (Zakhari, S. "Overview: How is Alcohol Metabolized by the Body?" Alcohol Research & Health, 29, 4, 2006, 245-255). Alcohol induced derangements of hepatic lipid metabolism results in steatosis. Initially the primary reason was thought to be redox shifts generated by the oxidation of ethanol by alcohol and aldehyde dehydrogenases that eventually inhibit beta oxidation caused by accumulation of NADH and product inhibition of the mitochondrial fatty acid-oxidizing dehydrogenases. Later on many new mechanisms for alcoholic steatosis have been suggested which are interrelated and provide a more comprehensive picture of how alcohol abuse deranges hepatic lipid metabolism and results in steatosis. These include oxidative stress, mobilization of peripheral triglyceride from the adipose tissue to the liver, alterations of transcriptional controls of lipid metabolism and increased hepatic lipid synthesis in responses to alcohol (Sozio M and Crabb D W. "Alcohol and Lipid Metabolism.", Am J Physiol Endocrinol Metab, 295, 1, 2008, E10-E16).

Liver and Immunological Factors

The forms of alcoholic liver diseases (ALD) are simple fatty liver (steatosis), fatty liver accompanied by inflammation (steatohepatitis) leading to scar tissue formation (fibrosis), and the destruction of the normal liver structure (liver cirrhosis), which may or may not improve with abstinence and subsequently might lead in liver cancer (hepatocellular carcinoma). Liver cirrhosis is the $12^{th}$ leading cause of death in United States. (Szabo, Gyongyi. "Alcohol and Health: Focus On: Alcohol and the Liver.", National Institute of Alcohol Abuse and Alcoholism, 40, 2010, 87-96).

Another plausible pathway of alcohol induced hepatotoxicity includes excess production of pro-inflammatory cytokines by gut-endotoxin stimulated Kupffer cells. ROS is mainly generated in association with the mitochondrial electron transport system; it is also produced by CYP2E1 and by activated Kupffer cells in the liver. Both acute and chronic alcohol consumption can increase ROS.

The mechanisms for the progression of alcohol induced liver injury are complex and dynamically regulated over time and hepatocellular location. Multiple mechanisms of cellular injury are involved during development of alcohol induced liver diseases. Programmed cell death or apoptosis is one of the major modes of hepatic cell death during alcohol liver diseases (Elmore, S. "Apoptosis: A Review of Programmed Cell Death.", Toxicologic Pathology, 35, 4, 2007, 495-516). Apart from apoptosis, there are two types of cell death, which have been described: necrosis and necroptosis (Zhang, et al. "RIP3, an Energy Metabolism That Switches TNF-Induced Cell Death from Apoptosis to Necrosis." Science, 325, 5938, 2009, 332-336) which are caused due to cascade of reaction, based on the activity of immune mediators. The liver acts as a vital immune organ comprising a large pool of natural killer cells and Kupffer cells, factors to initiate and propagate immune reactions (Gao et al. "Liver: An Organi with Predominant Innate Immunity." Hepatology, 47, 2, 2008, 729-36). Kupffer cell activation plays a pivotal role in alcoholic liver disease. A series of soluble innate immune factors and mediators including pro-inflammatory cytokines also play a crucial role in the development of alcohol induced liver diseases. Several pro-inflammatory cytokines are upregulated in the liver in response to alcohol exposure. Among them TNF-α, secreted from Kupffer cells, is a critical mediator (Wang, G., Manning, M L, and Amack J D. "Regional Shape Changes Control Form and Function of Kupffer's Vesicle in the Zebrafish Embryo." Dev Biol, 370, 1, 2012, 52-62). Production of TNF-α has also been stimulated by exposure of Lipopolysaccharide (LPS). Apart from TNF-α, IL-1β is another potent component that triggers liver damage.

Interleukin-22 (IL-22), cytokine that is produced by Th17 and NK cells, plays an important role in ameliorating alcoholic liver injury, controlling bacterial infection, homeostasis, and tissue repair. (Sung Hwan K et al., Interleukin-22 treatment ameliorates alcoholic liver injury in a murine model of chronic-binge ethanol feeding: Role of STAT3, Hepatology, 52, 4, 2010, 1291-1300).

IL-17 has been reported to play role in Human alcoholic liver disease, which is characterized by the activation of the IL-17 pathway by liver infiltration with IL-17-secreting cell infiltrates as a key feature that might contribute to liver neutrophil recruitment. (Arnaud Lemmers et al., The Interleukin-17 Pathway Is Involved in Human Alcoholic Liver Disease, 49, 2, 2008, 646-657.

Description of the Related Art

Liquor (alcoholic beverage) is a beverage containing ethyl alcohol. The functional alcoholic beverage of the present invention includes liquor so that the final alcohol concentration is 1.0-50.0%. The following prior art exists in the field of this invention:

WO1989004165A1 or EP0336960A4 divulges alcoholic beverages with combination of any one or more sugars from the group consisting of D-galactose, D-lactose, D-xylose, L-fructose, D-mannitol, sorbitol, D-glucose etc.

JP06014746 discloses alcoholic beverages comprising a glycoside of quercetin, divalent metallic ion and licorice extract (Glycyrrhizin). This beverage enhances alcohol metabolism and has hepatopathy-suppressive activity, due to ethanol and acetaldehyde. Thus, it reduces veisalgia.

WO2002017939 discloses Glycyrrhizaglabra, (glycyrrhizin), which facilitates the absorption and enhance uptake of herbal extracts, variety of drug molecules from anti-infective and anti-cancer category, nutraceutical compounds.

CN 1736270 discloses a liver-protecting drink constituting Chitosan oligosaccharide, glycyrrhizin, aqueous extract of kudzuvine flower and aqueous extract of hovenine.

JP2008266203 and EP0502554 discloses an increase in amount of an enzyme activity of the Reactive oxygen species (ROS) scavenging enzyme group such as superoxide dismutase, catalase or peroxidase with one or more kinds of substances selected from the group consisting of erythritol, mannitol, sorbitol and xylitol.

U.S. Pat. No. 4,987,123 A unveil an amino acid or oligopeptide containing either a L-alanine residue or a L-glutamine residue, or both in the therapy or prevention of alcoholic hepatic disorders.

Japanese Patent JP2000072669 divulges specific composition of amino acids and trehalose combination, which compensates the decrease in blood amino acids due to hard physical exercise and fatigue.

Japanese Patent JP63036773A discloses an alcoholic drink having excellent taste, flavour, nutrient and stability over a long period, which mainly contains amino acid such as glycine, alanine, tyrosine, etc., and sugar such as sorbitol, sucrose, fructose, etc.

CN 103404934 A unveil beverage consisting glutamine, alanine, methionine, ganoderan, vitamin C, maltitol, citric acid, and beta-cyclodextrin, which protects from Veisalgia, stomach and liver, promoting urination and improving immunity.

U.S. Pat. No. 6,713,091 B1 reveals composition amino acid & liquorice lowering the concentration of alcohol in blood.

CN 103445175A discloses composition comprising of synanthrin, xylitol, aminopropionic acid, alanine, and glutamine. This alleviates Veisalgia and protects liver.

CN 101332289A discloses liquorice extract, field turnip extract, fresh ginger extract, amino acid, vitamin, taurine, folic acid, calcium, magnesium, zinc and kalium. This formulation protects the liver from alcohol toxicity.

WO/2014/177989 is Applicant's own patent application and discloses reduced toxicity of functional alcoholic beverage comprising 18β-Glycyrrhizin or 18α-Glycyrrhizin and a sugar alcohol or sugars as synergistic hepato-protectants.

CN 103622981A discloses an invention containing glycyrrhizin, cysteine hydrochloride (amino), glycine (amino) and a pharmaceutic adjuvant like mannitol (sugar alcohol). The ratio of glycyrrhizin to cysteine hydrochloride to glycine is 1:1:1 for liver disease dermatology field, the field of cancer chemotherapy protection and other diseases.

CN 1706394A discloses ammonium glycyrrhizinate, cysteine hydrochloride, glycine, sodium bisulfite, and mannitol in certain proportion for skin disease and viral disease.

CN 1985987B relates synergistic combination 150 parts diammoniumlicorice and glutathione 300 copies in treating liver diseases, high stability, and wide application.

CN 1709272A invention reveals diammoniumglycyrrhizinate, cystine, glycine, methionine and vitamin B1 for curing the liver diseases & improving function of liver and cholestasis in the liver. It could also be used for auxiliary therapy of alcoholism and barbitones and sulfonamides drug poisoning. The combination ratio for diammoniumlicorice, cysteine and glycine is 3 to 5:2 to 4.30:50.

CN101633683 discloses 18-alpha or 18-beta glycyrrhizin, L-glutamic acid & mannitol for anti-hepatitis drug.

CN101669962A discloses 18-alpha and 18-beta glycyrrhizin (ratio 1 to 20:1), amino acid & xylitol based on literature claim for anti-inflammation, anti-anaphylaxis, oxidation resistance, anti-atherosclerosis, immune regulation and detoxification.

CN 1586489A unveils salts of glycyrrhizinate, amino acid(s), antioxidant stabilizer(s) to improve product stability.

CN102302502 invention reveals combination of various amino acid with glycyrrhizin. U.S. Pat. No. 4,987,123 comprising L-alanine and L-glutamine available in molar ratio of 1:0.1 to 1:10 or oligopeptide for hepatic disorders.

US 20100234308 discloses oligopeptide Alanylglutamine, a dipeptide containing two amino acids, alanine and glutamine. Each may be L- or D-forms, and the L-forms are preferred for wake up remedy.

U.S. Pat. No. 4,596,825 molar ratio of ornithine to alanine in said mixture is about 1:0.001 to 10, amount effective to prevent or alleviate said alcoholic liver disturbance. US2010/0086666 A1 reveals alcohol infused with protein like casein hydrolysate.

However, none of the prior art references, discloses, or teaches combining a composition of saponin glycosides such as liquorice or glycyrrhizin or glycyrrhizin derivative or its pharmaceutically acceptable salts, a sugar alcohol or sugar and, an Amino-Acid Derivative amino-acid or peptide residue, with distilled alcohol and deionized water.

Also, none of the prior art discloses or teaches a combination for modulating the immunology response, and thereby alleviating CNS stress.

In addition, none of the prior art discloses or teaches a synergistic composition for alleviating of hepatic stress. Further, none of the prior art discloses or teaches a synergistic composition modulating immunology parameter, alleviating oxidative stress and veisalgia.

OBJECTS OF THE INVENTION

The primary object of the invention is to provide a synergistic beverage composition for alleviating alcohol-induced oxidative stress, hepatic stress, CNS stress, veisalgia.

Another object of the invention is to provide a synergistic beverage composition for modulating immunology parameters of the human body.

A further object of the invention is to provide a method for the preparation of such synergistic composition.

SUMMARY OF THE INVENTION

Accordingly, there is provided a synergistic beverage composition for alleviating alcohol-induced oxidative stress, hepatic stress, CNS stress, veisalgia and modulating immunology parameters. The composition of the invention effectively alleviates alcohol-induced physiological and psychological effects, more particularly alleviating oxidative stress, hepatic stress, CNS stress, modulating immunology parameter and alleviating veisalgia.

The combination of Amino-Acid Derivative, a sugar alcohol or sugar, and Saponin glycoside at calculated proportions in the alcohol exhibits a synergistic effect which alleviates oxidative stress, hepatic stress, CNS stress, modulates immunology parameter, and alleviates veisalgia. Another benefit that has been observed is that sequential consumption of the synergistic composition simultaneously with alcohol improves the physiological and psychological parameters, bringing them closer to normal values. Yet another unexpected benefit is that the toxicity of the alcoholic beverage embodiment is significantly reduced.

In an exemplary embodiment of the invention, a synergistic beverage composition for alleviating alcohol-induced oxidative stress, hepatic stress, CNS stress, veisalgia and modulating immunology parameters is disclosed which comprises a saponin glycoside in a mass concentration range of 0.01 to 0.5%; an Amino-Acid derivative in a mass concentration range of 0.04 to 3.0%; and a sugar or sugar alcohol or combination thereof in a mass concentration range of 0.5 to 3.0%.

The saponin glycoside disclosed above may comprise Glycyrrhizin (GA) or Glycyrrhizin (GA) salt, or a combination of Glycyrrhizin (GA) and Glycyrrhizin (GA) salt, wherein the Glycyrrhizin (GA) may be selected from 18-β-Glycyrrhizin and 18-α-Glycyrrhizin. Glycyrrhizin (GA) may be a combination of 18-β-Glycyrrhizin and 18-α-Glycyrrhizin. The Glycyrrhizin (GA) salt comprises 18-α-Glycyrrhizin mono ammonium salt, 18-β-Glycyrrhizin mono ammonium salt, or a combination of 18-α-Glycyrrhizin mono ammonium salt and 18-β-Glycyrrhizin mono ammonium salt. In one preferred embodiment the saponin glycoside may be used in a mass concentration range of 0.04 to 0.5%.

When a combination of 18-β-Glycyrrhizin and 18-α-Glycyrrhizin is used such combination comprises equal parts of 18-β-Glycyrrhizin and 18-α-Glycyrrhizin.

When a combination of 18-α-Glycyrrhizin mono ammonium salt and 18-β-Glycyrrhizin mono ammonium salt is used such combination comprises equal parts of 18-α-Glycyrrhizin mono ammonium salt and 18-β-Glycyrrhizin mono ammonium salt.

The Amino-Acid derivative of the invention may be selected from the group of an amino-acid monomer, a dipeptide, a tripeptide, an oligopeptide, a protein and protein hydrolysate.

The amino-acid monomer may be selected from alanine, glutamine, arginine, ornithine, arginine pryoglutamate, asparaginine, L-Aspartic acid, D-Asparatic acid, L-Carnitine, citruline, cysteine, cystine, γ-amino butyric acid (GABA), glutathione, glycine, histidine, L-isoleucine, L-leucine, L-lysine, methionine, phenylalanine, L-proline, pyroglutamate, serine, taurine, threonine, tyrptophan, tyrosine, L-valine, and L-Theanine, or a combination of any of these two or more.

The dipeptide (DP) may be selected from L-alanyl-L-glutamine (L-Ala-L-Gln), glycyl-glycine (Gly-Gly) and L-glutamyl-L-alanine (Glu-Ala), or a combination of any of these two or more.

The oligopeptide may be selected from Oxidised L-Glutathione, Reduced L-Glutathione and Glutathione or a combination of any of these two or more.

In one preferred embodiment the Amino-Acid derivative is used in a mass concentration range of 0.5 to 3.0%.

The sugar of the composition may be selected from D-Maltodextrin, L-Maltodextrin, D-Maltose, L-Maltose, D-Dextrose, L-Dextrose, D-Glucose, L-Glucose, D-Trehalose, L-Trehalose, D-Sucrose, L-Sucrose, D-Lactose, L-Lactose, Hydrogenated Starch Hydrolysates, D-Fructose and D-Galactose, or a mixture of any of these two or more.

The sugar alcohol of the invention may be selected from D-Glycerol, L-Glycerol, D-Mannitol, L-Mannitol, D-erythritol, L-erythritol, D-xylitol, or L-xylitol, L-Maltitol, D-Maltitol, L-Sorbitol, D-Sorbitol, L-Lactitol, D-Lactitol, L-Isomalt and D-Isomalt, or a mixture of any of these two or more. In one preferred embodiment, the sugar alcohol is D-Mannitol or L-Mannitol and preferably the sugar alcohol is used in a mass concentration range of 0.5 to 2.5%.

The composition of the invention may also have pH adjusting agent and flavouring agent, wherein the pH adjusting agent may be selected from potassium sorbate (KS), monobasic sodium phosphate, dibasic sodium phosphate and tribasic sodium phosphate. In one preferred embodiment the pH adjusting agent is potassium sorbate (KS) present preferably in a mass concentration range of 0.01 to 0.2%.

The flavouring agent may be selected from extracts of herbs, spices, fruit, and artificial flavour, and used in mass concentration range of 0.01 to 0.2%.

A person skilled in the art would be able to arrive at many compositions which can be prepared within the ambit of the invention to obtain the optimum results in alleviating alcohol-induced oxidative stress, hepatic stress, CNS stress, veisalgia and modulating immunology parameters. Some of the preferred compositions showing best results in above physiological and psychological parameters are listed below. However, such list is only representative and not exhaustive.

a. 18-α-GA or 18-β-GA, in a mass concentration of 0.04%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1%;

b. 18-α-GA or 18-β-GA in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1%;

c. 18-α-GA or 18-β-GA in a mass concentration of 0.04%, %, D-Xylitol, L-Xylitol, D-Mannitol or L-Mannitol in a mass concentration of 2.5%, and L-alanyl-L-glutamine (L-Ala-L-Gln) or oxidised L-glutathione in a mass concentration of 1%;

d. 18-α-GA or 18-β-GA in a mass concentration of 0.04%, D-Xylitol, L-Xylitol, D-Mannitol or L-Mannitol in a mass concentration of 0.5%, and L-alanyl-L-glutamine (L-Ala-L-Gln) or oxidised L-glutathione in a mass concentration of 0.5%;

e. 18-α-GA or 18-β-GA in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 0.5%;

f. 18-α-GA or 18-β-GA in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 3.0%;

g. 18-α-GA or 18-β-GA in a mass concentration of 0.15%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.0%;

h. 18-α-GA or 18-β-GA in a mass concentration of 0.3%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.0%;

i. 18-α-GA or 18-β-GA in a mass concentration of 0.1%, D-Xylitol, L-Xylitol, D-Mannitol or L-Mannitol in a mass concentration of 2.5%, and L-alanyl-L-glutamine (L-Ala-L-Gln) or oxidised L-glutathione in a mass concentration of 1.0%;

j. 18-α-GA or 18-β-GA in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.25%;

k. 18-α-GA or 18-β-GA in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 2.0%;

l. 18-α-GA or 18-β-GA in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.5%;

m. 18-α-GA or 18-β-GA in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.25%;

n. 18-α-GA or 18-β-GA in a mass concentration of 0.1%, D-Xylitol, L-Xylitol, D-Mannitol or L-Mannitol in a mass concentration of 1.2%, and casein hydrosylate protein in a mass concentration of 1.0%;

o. 18-α-GA or 18-β-GA in a mass concentration of 0.1%, D-Xylitol, L-Xylitol, D-Mannitol or L-Mannitol in a mass concentration of 1.2%, and casein hydrosylate protein in a mass concentration of 2.0%;

p. 18-α-GA in a mass concentration of 0.05%, 18-β-GA in a mass concentration of 0.05%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.0%;

q. 18-α-GA in a mass concentration of 0.05%, 18-β-GA in a mass concentration of 0.05%, D-Xylitol, L-Xylitol, D-Mannitol or L-Mannitol in a mass concentration of 1.2%, and oxidised L-glutathione in a mass concentration of 1.0%;

r. equal parts 18α-GA and 18-β-GA in a combined mass concentration range of 0.04 to 0.1%, a sugar alcohol selected from the group consisting of D-Xylitol, L-Xylitol, D-Mannitol, and L-Xylitol in a mass concentration range of 0.5 to 2.5%, and a dipeptide comprising L-alanyl-L-glutamine (L-Ala-L-Gln) or oxidised L-glutathione in a mass concentration range of 0.5 to 3.0%; and s. saponin glycoside comprising 18α-GA or 18-β-GA, or a combination thereof, in a mass concentration range of 0.04 to 0.1%, a sugar alcohol selected from the group consisting of D-Xylitol, L-Xylitol, D-Mannitol, and L-Xylitol in a mass concentration range of 0.5 to 2.5%, and a dipeptide comprising L-alanyl-L-glutamine (L-Ala-L-Gln) or oxidised L-glutathione in a mass concentration range of 0.5 to 3.0%.

In one embodiment, the invention provides a synergistic beverage composition for alleviating alcohol-induced oxidative stress, hepatic stress, CNS stress, veisalgia and modulating immunology parameters comprising:
(a) a saponin glycoside comprising 18-β-glycyrrhizin, 18-α-glycyrrhizin, or a combination thereof, in a mass concentration range of 0.04 to 0.5%;
(b) an amino-Acid derivative comprising a dipeptide (DP) L-alanyl-L-glutamine (L-Ala-L-Gln) and an oligopeptide oxidised L-Glutathione in a mass concentration range of 0.04 to 3.0%;
(c) a sugar alcohol comprising mannitol, xylitol or erythritol, in a mass concentration range of 0.5 to 3.0%;
(d) quantum sufficit (qs) distilled alcohol or a combination of deionized water and distilled alcohol; and
(e) optionally, a pH adjusting agent potassium sorbate (KS) in a mass concentration range of 0.01 to 0.2%, and a flavouring agent in a mass concentration range of 0.01 to 0.2%.

In another embodiment, the invention provides a synergistic beverage composition for alleviating alcohol-induced oxidative stress, hepatic stress, CNS stress, veisalgia and modulating immunology parameters comprising:
(a) 18-β-Glycyrrhizin in a mass concentration range of 0.04 to 0.3%;
(b) D-mannitol in a mass concentration range of 0.1 to 2.5%; and
(c) Oxidised L-glutathione in a mass concentration range of 0.5 to 2.0%.

In a further embodiment, the invention provides a synergistic beverage composition for alleviating alcohol-induced oxidative stress, hepatic stress, CNS stress, veisalgia and modulating immunology parameters comprising:
(a) 18-β-Glycyrrhizin in a mass concentration range of 0.04 to 0.3%;
(b) D-mannitol in a mass concentration range of 0.5 to 2.5%; and
(c) L-alanyl-L-glutamine in a mass concentration range of 0.5 to 2.0%.

DETAILED DESCRIPTION OF THE INVENTION

The present invention relates to a composition for alcoholic beverage for alleviating oxidative stress, hepatic stress, CNS stress, modulating immunology parameters, and alleviating veisalgia resulting from alcohol consumption. The invention also provides a process for the preparation of said alcoholic beverage composition.

In one aspect, the present invention provides a synergistic beverage composition comprising following ingredients
a saponin glycoside
an Amino-Acid Derivative,
a sugar alcohol or sugar,
water and
alcohol.

Amino-Acid Derivatives: a molecule consisting of one or more amino-acid molecules, such as an amino-acid monomer, dipeptide, tripeptide, oligopeptide, polypeptide, protein or a peptide hydrolysate or a peptide residue thereof.

Saponin Glycoside: such as Glycyrrhizin, including a derivative or its isomer, such as 18α-Glycyrrhizin, 18β-Glycyrrhizin, 18α-mono ammonium glycyrrhizinate, 18β-mono ammonium glycyrrhizinate, or a combination thereof.

Sugar: Compounds such as D-Maltodextrin, L-Maltodextrin, D-Maltose, L-Maltose, D-Dextrose, L-Dextrose, D-Glucose, L-Glucose, D-Trehalose, L-Trehalose, D-Sucrose, L-Sucrose, D-Lactose, L-Lactose, Hydrogenated Starch Hydrolysates, D-Fructose, D-Galactose, or mixture thereof.

Sugar alcohol: Compounds such as, D-Glycerol, L-Glycerol, D-Mannitol, L-Mannitol, D-erythritol, L-erythritol, D-xylitol, or L-xylitol, L-Maltitol, D-Maltitol, L-Sorbitol, D-Sorbitol, L-Lactitol, D-Lactitol, L-Isomalt, D-Isomalt or mixture thereof.

In the above beverage composition, the combination of active ingredients such as—a saponin glycoside, an Amino-Acid Derivative, and a sugar alcohol or sugar at appropriate concentrations/proportions/amounts exhibits synergistic activity, effectively alleviating alcohol-induced physiological and psychological effects, more particularly alleviating oxidative stress, hepatic stress, CNS stress, modulating immunology parameter, and alleviating veisalgia.

The beverage composition of the present invention may be other than alcoholic beverage also. In such a case when the above beverage composition of the present invention is not an alcoholic beverage, the above beverage composition does not comprise alcohol and alcohol is replaced with a suitable potable liquid such as deionized water. In this case also the beverage composition exhibits similar synergistic effects in alleviating oxidative stress, hepatic stress, CNS stress, modulating immunology parameter, and alleviating veisalgia. The stress may arise from either alcohol consumption or any other reasons.

In one preferred embodiment of the present invention, the beverage composition is an alcoholic beverage composition comprising alcohol as a liquid to be drink.

The above beverage composition of the present invention comprises a saponin glycoside in a mass concentration range of 0.01 to 0.5%; an Amino-Acid derivative in a mass concentration range of 0.04 to 3.0%; and a sugar or sugar alcohol or combination thereof in a mass concentration range of 0.5 to 3.0%.

The saponin glycoside disclosed above may comprise Glycyrrhizin (GA) or Glycyrrhizin (GA) salt, or a combination of Glycyrrhizin (GA) and Glycyrrhizin (GA) salt, wherein the Glycyrrhizin (GA) may be selected from 18-β-Glycyrrhizin and 18-α-Glycyrrhizin. Glycyrrhizin (GA) may be a combination of 18-β-Glycyrrhizin and 18-α-Glycyrrhizin. The Glycyrrhizin (GA) salt comprises 18-α-Glycyrrhizin mono ammonium salt, 18-β-Glycyrrhizin mono ammonium salt, or a combination of 18-α-Glycyrrhizin mono ammonium salt and 18-β-Glycyrrhizin mono ammonium salt. In one preferred embodiment the saponin glycoside may be used in a mass concentration range of 0.04 to 0.5%.

When a combination of 18-β-Glycyrrhizin and 18-α-Glycyrrhizin is used such combination comprises equal parts of 18-β-Glycyrrhizin and 18-α-Glycyrrhizin.

When a combination of 18-α-Glycyrrhizin mono ammonium salt and 18-β-Glycyrrhizin mono ammonium salt is used such combination comprises equal parts of 18-α-Glycyrrhizin mono ammonium salt and 18-β-Glycyrrhizin mono ammonium salt.

Under appropriate circumstances, as will be understood by one with ordinary skill in the art, it may be desirable to include a different phytoconstituent extracted from *glycyrrhiza glabra* instead of glycyrrhizin, such as liquiritin or another flavonoid, to achieve similar desirable effects.

The above said "Amino-Acid Derivative" comprises an amino acid monomer, polypeptides and/or oligopeptides such as dipeptides, tripeptides, tetrapeptides etc., protein, or a peptide hydrolysate or a peptide residue thereof.

The above said amino acid monomer comprises alanine, glutamine, arginine, or ornithine. Under appropriate circumstances, as will be understood by one of ordinary skill in the art, in order to help achieve the above-mentioned benefits, it is desirable to include a different or additional amino acid monomer, such as arginine, arginine pryoglutamate, asparaginine, L-Aspartic acid, D-Asparatic acid, L-Carnitine, citruline, cysteine, cystine, Gamma-amino butyric acid (GABA), glutathione, glycine, histidine, L-isoleucine, L-leucine, L-lysine, methionine, phenylalanine, L-proline, pyroglutamate, serine, taurine, threonine, tyrptophan, tyrosine, L-valine, or L-Theanine, L-Lysine HCl or a combination thereof, to achieve similar desirable effects.

The above said peptide residue, comprises a dipeptide residue, tripeptide residue, other oligopeptide residue, or polypeptide residue. Under appropriate circumstances, as will be understood by one of ordinary skill in the art, in order to help achieve the above-mentioned benefits, it is desirable to include a different or additional amino acid monomer, such as L-Lysine HCl, L-IsoLeucine, L-Leucine, L-valine, L-Proline, L-Aspartic acid.

The above said dipeptide (DP) comprises L-alanyl-L-glutamine (L-Ala-L-Gln). Under appropriate circumstances, as will be understood by one with ordinary skill in the art will understand, in order to help achieve the above-mentioned benefits, it is desirable to include a different dipeptide to achieve similar desirable effects, such as glycyl-glycine (Gly-Gly) or L-glutamyl-L-alanine (Glu-Ala).

The above said oligopeptide comprises glutathione (L-Glutamyl-L-Cysteinyl-Glycine, Glu-Cys-Gly). The glutathione may be in its reduced form with a free thiol group (GSH) or in its oxidised form with a disulfide bond (GSSG). In one preferred embodiment, the oligopeptide is oxidised glutathione (GSSG). Under appropriate circumstances, as will be understood by one with ordinary skill in the art, in order to help achieve the above-mentioned benefits, it is desirable to include a different oligopeptide such as glutathione oxidised or reduced or Peptide T.

The above said Amino-Acid Derivative also includes a protein such as casein or sodium caseinate whey. Under appropriate circumstances, as will be understood by one with ordinary skill in the art, in order to help achieve the above-mentioned benefits, it is desirable to include a different protein, such as casein hydrolysate, whey hydrolysate.

The above said sugar alcohol includes D-Mannitol, L-Mannitol, D-sorbitol, L-sorbitol, D-erythritol, D-xylitol, L-xylitol or mixture thereof. Under appropriate circumstances, as will be understood by one with ordinary skill in the art, in order to help achieve the above-mentioned benefits, it is desirable to include a combination of two or more the aforementioned sugar alcohols.

The above said sugar includes D-Xylose, D-Mannose, D-Sucrose, D-Lactose or mixture thereof. Under appropriate circumstances, as will be understood by one with ordinary skill in the art, in order to help achieve the above-mentioned benefits, it is desirable to include a combination of two or more of the aforementioned sugars.

In one embodiment of the present invention, the beverage composition comprises only one sugar alcohol or sugar. In another embodiment of the present invention, the beverage composition comprises mixture of two or more sugar alcohol(s) and/or sugar(s). Preferably the beverage composition comprises sugar alcohols such as Mannitol (D or L) or Xylitol (D or L) or D-Erythritol. In one preferred embodiment, the sugar alcohol present in the beverage composition is D-Mannitol. In another preferred embodiment, the sugar alcohol present in the beverage composition is D-Xylitol. In another preferred embodiment, the sugar alcohol present in the beverage composition is D-Erythritol.

The water is deionized water and the alcohol is distilled alcohol. The distilled alcohol may be aqueous distilled alcohol. The quantities of both the water and alcohol are quantity sufficient (qs) and are added to make the beverage composition 100%.

Optionally, the above said beverage composition of the present invention further comprises other non-active ingredients such as one or more pH adjusting agent(s) and/or one or more flavouring agent(s) each present in an amount ranging from in a mass concentration range of about 0.01 to 0.2%.

The pH adjusting agent is an organic or inorganic base/buffer, preferably selected from potassium sorbate (KS) or sodium phosphate (monobasic or dibasic or tribasic). In one embodiment, the pH adjusting agent is potassium sorbate (KS) present in a mass concentration range a range of about 0.01 to 0.2%. In one embodiment the amount of KS in the beverage composition is in a mass concentration range 0.1%.

The one or more flavouring agent to impart/improve taste/odour of the beverages may be natural flavouring agents such as extracts of herbs, spices or fruit; or artificial or palatable synthetic flavouring agents present in a mass concentration range of about 0.01 to 0.2%. In one embodiment the flavouring agent is selected from vanilla and strawberry. In one embodiment, the beverage composition does not comprise any flavouring agent.

In one embodiment the beverage composition of the present invention comprises:
glycyrrhizin (GA) or its derivatives or its pharmaceutically salt in a mass concentration range of 0.01 to 0.5%,
a peptide or peptide residue in a mass concentration range of 0.04 to 3.0%,
a sugar alcohol or sugar in a mass concentration range of 0.5 to 3.0%,
a quantum sufficit (qs) of deionized water,
a quantum sufficit (qs) of distilled alcohol,
optionally, pH adjusting agent(s) in a mass concentration range of 0.01 to 0.2%, and
optionally, flavouring agent(s) in a mass concentration range of 0.01 to 0.2%.

In another embodiment the beverage composition of the present invention comprises:
glycyrrhizin (GA) or its derivatives or its pharmaceutically salt in a mass concentration range of 0.01 to 0.5%,
a dipeptide (DP) in a mass concentration range of 0.04 to 3.0%,
a sugar alcohol or sugar in a mass concentration range of 0.5 to 3.0%,
a quantum sufficit (qs) of deionized water,
a quantum sufficit (qs) of distilled alcohol,
optionally, pH adjusting agent(s) in a mass concentration range of 0.01 to 0.2%, and
optionally, flavouring agent(s) in a mass concentration range of 0.01 to 0.2%.

In another embodiment the beverage composition of the present invention comprises:
glycyrrhizin (GA) or its derivatives or its pharmaceutically salt in a mass concentration range of 0.01 to 0.5%,
an oligopeptide in a mass concentration range of 0.04 to 3.0%,
a sugar alcohol or sugar in a mass concentration range of 0.5 to 3.0%,
a quantum sufficit (qs) of deionized water,
a quantum sufficit (qs) of distilled alcohol,
optionally, pH adjusting agent(s) in a mass concentration range of 0.01 to 0.2%, and
optionally, flavouring agent(s) in a mass concentration range of 0.01 to 0.2%.

In another embodiment the beverage composition of the present invention comprises:
glycyrrhizin (GA) or its derivatives or its pharmaceutically salt in a mass concentration range of 0.01 to 0.5%,
a protein in a mass concentration range of 0.04 to 3.0%,
a sugar alcohol or sugar in a mass concentration range of 0.5 to 3.0%,
a quantum sufficit (qs) of deionized water,
a quantum sufficit (qs) of distilled alcohol,
optionally, pH adjusting agent(s) in a mass concentration range of 0.01 to 0.2%, and
optionally, flavouring agent(s) in a mass concentration range of 0.01 to 0.2%.

In any of the above presented embodiments, the concentrations/amounts of active ingredients are in effective amount within the mentioned range.

In the above said embodiments—
the glycyrrhizin (GA) or its derivatives or its pharmaceutically acceptable salt, peptide or peptide residue, dipeptide (DP), tripeptide (TP), oligopeptide, protein, sugar alcohol or sugar are any of all as defined in above paragraphs and/or as defined below.
the glycyrrhizin (GA) may be 18α-GA or 18β-GA or combination of both. In one preferred embodiment the GA is 18α-GA. In another preferred embodiment the GA is β-GA. In another preferred embodiment the GA is equal part combination of both α-GA and β-GA. In another embodiment, the Glycyrrhizin is Glycyrrhizin salt, such as mono ammonium 18α-GA, 18β-GA, or a combination of mono ammonium 18α-GA and mono ammonium 18β-GA.
the dipeptide (DP) may be selected from L-Ala-L-Gln, Gly-Gly and Glu-Ala; more preferably the DP is L-Ala-L-Gln.
the oligopeptide is glutathione (Glu-Cys-Gly), preferably oxidised glutathione (GSSG).
the protein is selected from casein hydrolysate (hydrolyzed Casein Protein), whey hydrolysate (hydrolyzed Whey Protein), preferably the protein is hydrolyzed Casein Protein (CP).

The sugar alcohol may be selected from D-Mannitol, L-Mannitol, D-sorbitol, L-sorbitol, D-erythritol, D-xylitol, L-xylitol or mixture of two or more thereof; preferably the sugar alcohol is Mannitol (D or L) or Xylitol (D or L). In one preferred embodiment, the sugar alcohol is D-Mannitol. In another embodiment, the sugar alcohol is D-Xylitol.

The sugar may be selected from D-Maltodextrin, L-Maltodextrin, D-Maltose, L-Maltose, D-Dextrose, L-Dextrose, D-Glucose, L-Glucose, D-Trehalose, L-Trehalose, D-Sucrose, L-Sucrose, D-Lactose, L-Lactose, Hydrogenated Starch Hydrolysates, D-Fructose, D-Galactose, or mixture thereof.

The combinations of above said three main ingredients viz. glycyrrhizin (GA) or its derivatives or its salt, Amino-Acid Derivative such as amino acid monomer, peptide or peptide residue or protein and a sugar alcohol or sugar in the above described beverage compositions, exhibit synergistic effect in alleviating oxidative stress, hepatic stress, CNS stress, modulating immunology parameter, and alleviating veisalgia. The synergistic activity depends on the concentrations of each ingredient in the composition and appropriate concentrations of all the three main ingredients in the combination. At appropriate proportions/concentrations of all the three ingredients in a combination, the beverage composition shows maximum protection (%) and synergistic effect (%).

The combination of above said three main ingredients viz. glycyrrhizin (GA) or its derivatives or its salt, Amino-Acid Derivative such as amino acid monomer, peptide or peptide residue or protein and a sugar alcohol or sugar at appropriate effective concentrations/percentages/quantities/amounts in different combinations are further elaborated in below paragraphs.

Effective concentration/percentage/quantity/amount is the amount of each active agent that must be included in a beverage to result in a net CNS, hepatic or other protective synergistic effect. Effective amount include:

Saponin Glycoside such as Glycyrrhizin or its derivatives or its salt, in a mass concentration range between 0.01% to 0.5% or 0.03% to 0.3% or 0.04% to 0.1% or 0.1% to 0.3%. The amount of GA may be 0.01% or 0.02% or 0.03% or 0.04% or 0.05% or 0.06% or 0.07% or 0.08% or 0.09% or 0.1% or 0.11% or 0.115% or 0.12% or 0.125% or 0.13% or 0.135% or 0.014% or 0.15% or 0.16% or 0.17% or 0.18% or 0.19% or 0.2% or 0.25% or 0.3 or 0.35% or 0.4% or 0.45% or 0.5%.

Amino-Acid Derivative such as amino acid monomer, dipeptide or tripeptide or protein in a mass concentration range of 0.04% to 3.0% or 0.1 to 3.0% or 0.3 to 3.0% or 0.5 to 3% or 0.8 to 3.0% or 1.0 to 3.0% or 1.0 to 2.5% or 1.0 to 2.0%. The amount of Amino-Acid Derivative may be 0.1% or 0.15% or 0.2% or 0.25% or 0.3% or 0.35% or 0.4% or 0.5% or 0.6% or 0.7% or 0.8% or 0.9% or 1.0% or 1.15% or 1.2% or 1.25% or 1.3% or 1.35% or 1.5% or 2.0% or 2.5% or 3.0%.

Sugar alcohol such as Mannitol or Xylitol or sugar in a mass concentration range of 0.5% to 3.0% or 0.5 to 2.5% or 0.5 to 2.0% or 0.5 to 1.5% or 0.5 to 1% or 1.0 to 3.0% or 2.0 to 3.0%. The amount of sugar alcohol may be 0.5% or 0.6% or 0.7% or 0.8% or 0.9% or 1.0% or 1.1% or 1.12% or 1.13 or 1.14% or 1.15% or 1.16% or 1.17% or 1.18% or 1.19% or 1.2% or 1.25% or 1.3% or 1.4% or 1.45% or 1.5% or 1.55% or 1.6% or 1.65% or 1.7% or 1.75% or 1.8% or 1.85% or 1.9% or 2.0% or 2.1% or 2.2% or 2.3% or 2.4% or 2.5% or 2.6% or 2.7& or 2.8% or 2.9% or 3.0%.

Further the appropriate amounts of Saponin Glycoside, Amino-Acid Derivative and Sugar/Sugar Alcohol may be the amounts as depicted in tables 1-4 (below).

In one embodiment of the present invention the synergistic beverage composition comprises any one of below combination of active ingredients along with water and alcohol, optionally along with other non-active ingredients such as one or more pH adjusting agents and/or flavouring agents:

(a) α-GA or β-GA (0.04-0.1%)+L-Ala-L-Gln (≥1.0%)+D-Mannitol (2.5%)
(b) α-GA or β-GA (0.04-0.1%)+Oxidised Glutathione (≥2.0%)+D-Mannitol (1.2%)
(c) α-GA or β-GA (0.04-0.1%)+L-Ala-L-Gln (≥1.0%)+D-Mannitol (1.2%)
(d) α-GA or β-GA (0.04-0.1%)+hydrolysed Casein Protein (≥1.0%)+D-Mannitol (1.2%)

In another embodiment of the present invention the synergistic beverage composition comprises any one of below combination of active ingredients along with water and alcohol, optionally along with other non-active ingredients such as one or more pH adjusting agents and/or flavouring agents.

A person skilled in the art would be able to arrive at many compositions which can be prepared within the ambit of the invention to obtain the optimum results in alleviating alcohol-induced oxidative stress, hepatic stress, CNS stress, veisalgia and modulating immunology parameters. Some of the preferred compositions showing best results in above physiological and psychological parameters are listed below of active ingredients along with water and alcohol, optionally along with other non-active ingredients such as one or more pH adjusting agents and/or flavouring agents. However, such list is only representative and not exhaustive.

a. 18-α-GA or 18-β-GA, in a mass concentration of 0.04%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1%;

b. 18-α-GA or 18-β-GA in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1%;

c. 18-α-GA or 18-β-GA in a mass concentration of 0.04%, %, D-Xylitol, L-Xylitol, D-Mannitol or L-Mannitol in a mass concentration of 2.5%, and L-alanyl-L-glutamine (L-Ala-L-Gln) or oxidised L-glutathione in a mass concentration of 1%;

d. 18-α-GA or 18-β-GA in a mass concentration of 0.04%, D-Xylitol, L-Xylitol, D-Mannitol or L-Mannitol in a mass concentration of 0.5%, and L-alanyl-L-glutamine (L-Ala-L-Gln) or oxidised L-glutathione in a mass concentration of 0.5%;

e. 18-α-GA or 18-β-GA in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 0.5%;

f. 18-α-GA or 18-β-GA in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 3.0%;

g. 18-α-GA or 18-β-GA in a mass concentration of 0.15%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.0%;

h. 18-α-GA or 18-β-GA in a mass concentration of 0.3%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.0%;

i. 18-α-GA or 18-β-GA in a mass concentration of 0.1%, D-Xylitol, L-Xylitol, D-Mannitol or L-Mannitol in a mass concentration of 2.5%, and L-alanyl-L-glutamine (L-Ala-L-Gln) or oxidised L-glutathione in a mass concentration of 1.0%;

j. 18-α-GA or 18-β-GA in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.25%;

k. 18-α-GA or 18-β-GA in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 2.0%;

l. 18-α-GA or 18-β-GA in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.5%;

m. 18-α-GA or 18-β-GA in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.25%;

n. 18-α-GA or 18-β-GA in a mass concentration of 0.1%, D-Xylitol, L-Xylitol, D-Mannitol or L-Mannitol in a mass concentration of 1.2%, and casein hydrosylate protein in a mass concentration of 1.0%;

o. 18-α-GA or 18-β-GA in a mass concentration of 0.1%, D-Xylitol, L-Xylitol, D-Mannitol or L-Mannitol in a mass concentration of 1.2%, and casein hydrosylate protein in a mass concentration of 2.0%;

p. 18-α-GA in a mass concentration of 0.05%, 18-β-GA in a mass concentration of 0.05%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.0%;

q. 18-α-GA in a mass concentration of 0.05%, 18-β-GA in a mass concentration of 0.05%, D-Xylitol, L-Xylitol, D-Mannitol or L-Mannitol in a mass concentration of 1.2%, and oxidised L-glutathione in a mass concentration of 1.0%;

r. equal parts 18α-GA and 18-β-GA in a combined mass concentration range of 0.04 to 0.1%, a sugar alcohol selected from the group consisting of D-Xylitol, L-Xylitol, D-Mannitol, and L-Xylitol in a mass concentration range of 0.5 to 2.5%, and a dipeptide comprising L-alanyl-L-glutamine (L-Ala-L-Gln) or oxidised L-glutathione in a mass concentration range of 0.5 to 3.0%; and s. saponin glycoside comprising 18α-GA or 18-β-GA, or a combination thereof, in a mass concentration range of 0.04 to 0.1%, a sugar alcohol selected from the group consisting of D-Xylitol, L-Xylitol, D-Mannitol, and L-Xylitol in a mass concentration range of 0.5 to 2.5%, and a dipeptide comprising L-alanyl-L-glutamine (L-Ala-L-Gln) or oxidised L-glutathione in a mass concentration range of 0.5 to 3.0%.

The above mentioned combinations of three main active ingredients are non limiting and are illustrative. Without limiting with above, the beverage composition of the present invention may comprise any appropriate and effective amounts of said three active ingredients, which are capable to show greater protection and show greater synergism. Further the above combination of three active ingredients in the beverage composition optionally comprises appropriate amounts of pH adjusting agent(s) and flavouring agents(s).

To measure the % protection and % synergistic effect of the present synergistic beverage composition comprising combinations of saponin glycoside, Amino-Acid Derivative and sugar alcohol, different combinations with alterations in amount/quantity of each ingredients are tested and evaluated for its effects on Hangover, CNS, Immunology, Hepatoprotection and other activities taking different parameters. The results show excellent synergistic effect of combination of three active ingredients viz. Saponin glycoside, Amino-Acid-Derivative and sugar alcohol or sugar at effective concentrations/amounts as compared to effects of any single or combination of any two of the said active ingredients (Results in Tables 1-4 below).

While not necessary to an understanding of the composition and method for preparing or using of the composition, it is of illustrative benefit to first describe what appears to be the biochemical mechanism. Physiological changes during a state of veisalgia, in particular, nausea, headache, and fatigue have been suggested to be mediated by changes in immune system function. The immune response is triggered by several pro-inflammatory cytokines which are upregulated in the liver in response to alcohol exposure. Among them TNF-α, secreted from Kupffer cells, is a critical mediator. The values of the cytokines like Interleukin (IL), IL-10, IL-12 and IFN-α shows significant increase, 13 hours after alcohol consumption. An increase in production of IL-10, as a response to pro-inflammatory cytokine production, thus supports the suggestion of impaired cellular immunity during veisalgia. Glycyrrhizin inhibits HMGB1 and also acts as antoll-like receptor 4 (TLR4) antagonist as well as inhibitor of microglial activation all blocked ethanol-induced expression of pro-inflammatory cytokines like TNF-α and IL-1b.

Experimental Study and Evaluation:

A design of experiments ("DOE") methodology, a standard methodology of experimentation is used to obtain the maximum information from the minimum number of experiments, was employed to investigate the performance of the beverage composition for modulating immunology parameters, alleviating oxidative stress, hepatic stress, CNS stress and veisalgia. One or more parameters were selected to evaluate hangover related CNS symptoms. Some of these parameters are considered to be well correlated with hangover symptoms such as headache, cognitive deficit, impairment of memory etc. These are IL-12, CRP, HMGB1, MCP-1, IL-1beta, IL-10, WBC count (total & differential), serum acetate, acetylcholine esterase activity from brain homogenate, water maze experiment, rotarod test for motor coordination, spontaneous locomotor activity, etc. To evaluate alterations in liver functions, if any, it is essential to estimate serum ALT, AST, ALP and TNF-α.

The levels of IL-12 in serum were measured using commercial ELISA kit bought from Invitrogen (www.invitrogen.com) according to the manufacturer's protocols. The levels of HMGB1 and MCP-1 in serum were measured using commercial ELISA kit bought from Elabscience (www.elabscience.com) according to the manufacturer's protocols. The levels of C-reactive protein (CRP) in serum were measured using commercial ELISA kit bought from BD Biosciences (www.bdbiosciences.com) according to the manufacturer's protocols. The levels of acetate in serum were measured using commercial colorimetric assay kit bought from Sigma (www.sigmaaldrich.com), according to the manufacturer's protocols. The levels of alanine aminotransferase (ALT), aspartate aminotransferase (AST) and alkaline phosphatise (ALP) in serum were measured using commercial spectrophotometric kit bought from Span Diagnostic Ltd. (www.span.in) according to the manufacturer's protocols. The levels of TNF-α in serum were measured using commercial ELISA kit bought from Biolegend Inc. (www.biolegend.com) according to the manufacturer's protocols.

Several beverage compositions were prepared and evaluated for establishing alleviation of hepatic disorder, CNS disorder and veisalgia. The experimental models and the parameters used for evaluating these indications will be clear from the foregoing explanations.

The levels of IL-12 in serum were measured using commercial ELISA kit bought from Invitrogen (www.invitrogen.com) according to the manufacturer's protocols. The lowest detectable limit of the kit is <3 pg/ml (Trinchieri G. "Interleukin-12: A Cytokine at the Interface of Inflammation and Immunity." Adv. Immunol., 70, 1998, 83-243).

The levels of high mobility group box 1 ("HMGB1") in serum were measured using commercial ELISA kit bought from Elabscience (www.elabscience.com) according to the manufacturer's protocols. The lowest detectable limit of the kit is 18.75 pg/ml (Yamada et al. "HMGB1 Quantified by ELISA with a Monoclonal Antibody that Does Not Cross-React with HMGB2." Clin Chem, 49, 9, 1535-1537).

The levels of "MCP-1" in serum were measured using commercial ELISA kit bought from Elabscience (www.elabscience.com) according to the manufacturer's protocols. The lowest detectable limit of the kit is 0.1 ng/ml (Wang L, Li Y, Chen J, et al. "Ischemic Cerebral Tissue and MCP-1 Enhance Rat Bone Marrow Stromal Cell Migration in Interface Culture." Experimental Hematology, 30, 7, 2002, 831-836).

The levels of "CRP" in serum were measured using commercial ELISA kit bought from BD Biosciences (www.bdbiosciences.com) according to the manufacturer's protocols (Diaz P N, Bleeker, W K, Lubbers, Y, et al. "Rat C-Reactive Protein Activates the Autologous Complement System." Immunology, 58, 1, 2003, 186-195).

The levels of acetate in serum were measured using commercial colorimetric assay kit bought from Sigma (www.sigmaaldrich.com), according to the manufacturer's protocols (Nuutinen H, et al. "Elevated Blood Acetate as Indicator of Fast Ethanol Elimination in Chronic Alcoholics." Alcohol, 2, 4, 623-626).

The levels of "ALT" in serum were measured using commercial spectrophotometric kit bought from Span Diagnostic Ltd. (www.span.in) according to the manufacturer's protocols (Begmeyer H U and Bernt E, 1974, Methods of enzymatic analysis, VerlagChemie, Weinhelm, Academic press, London, New York, Vol 2, p 735).

The levels of "AST" in serum were measured using commercial spectrophotometric kit bought from Span Diagnostic Ltd. (www.span.in) according to the manufacturer's protocols (Tietz, Norbert W. Fundamentals of Clinical Chemistry. 3rd ed. Philadelphia: W.B. Saunders, 1970. 447. Print.).

The levels of alkaline phosphatise ("ALP") in serum were measured using commercial spectrophotometric kit bought from Span Diagnostic Ltd. (www.span.in) according to the manufacturer's' protocols (Varley, H., Gowenlock, A. H., and Bell, M. Practical Clinical Biochemistry. Vol I. Fifth edn. London: William Heinemann Medical Books Lts, 1980. 453. Print).

The levels of "TNF-α" in serum were measured using commercial ELISA kit bought from Biolegend Inc. (www.biolegend.com) according to the manufacturer's protocols. The lowest detectable limit of the kit is <5 pg/ml (In Immunoassay: A Practical Guide, Chan and Perlstein, Eds. Academic Press: New York, p 7.

Several studies indicated a relationship between higher cytokine level and memory impairments (Reichenberg et al., 2001, Arch Gen Psychiatry 58: 445-552 and Prat et al., 2008, Addict Behav 33: 15-23). Furthermore, high cytokine levels are related positively with the scores in a subjective hangover scale (Kim D J, Kim W, Yoon S J, et al. Effects of alcohol veisalgia on cytokine production in healthy subjects. Alcohol 2003; 31: 167-70). In the present study we estimated serum levels of IL-12 and CRP as a marker of hangover. In order to identify alteration of spatial learning, memory and performance changes Morris water-maze task has been carried out in experimental animals (Vorhees C V and Williams M T, 2006, Nat Protoc, 1, 848-58).

The neurotransmitter that has been implicated as most intricately involved in functions of memory storage, consolidation and recall is Acetylcholine ("Ach"). It is a key chemical messenger that controls cognitive processing as well as our basic thoughts. Optimal levels of Ach can contribute to better memory capacity, reasoning and logical thinking skills, creative thought, etc. Acetylcholinesterase is an enzyme that degrades ACh terminating the physiological action of the neurotransmitter. Higher level of brain acetylcholinesterase activity, particularly in cerebral cortex and hippocampus, disrupts cognition and memory functions because it hydrolyzes Ach before it reaches the receptor. Presences of higher concentrations of acetylcholinesterase in front of Ach-receptors facilitate termination of the signal transmission (Rico E P et al, 2007, Toxicology Letters, 174, 25-30; Vinod Tiwari et al, 2009, Behavioural Brain Research, 203, 296-303). We have included this parameter to evaluate cognition and memory deficit in experimental animals.

MCP-1 is a β-chemokine that specifically induces the chemotaxis and activation of mononuclear phagocytes. It is intimately involved in the inflammatory reaction by regulating the migration and survival of monocytes into tissues and their subsequent differentiation into macrophages. MCP-1 is produced by a number of cells, including endothelial cells, fibroblasts, monocytes, lymphocytes, smooth muscle cells and even tumor cells. An enhanced expression of MCP-1 was found in liver parenchymal cells at sites of inflammation in patients with alcoholic hepatitis (Afford S C et al., J Pathol, 186, 1998, 82-89) suggesting that MCP-1 may play an important role in the stimulation of the inflammatory infiltrate, induce enhanced expression of adhesion molecules in monocytes and promotion of a pro-inflammatory cytokine synthesis, thus amplifying the inflammatory cascade. Plasma MCP-1 concentrations are directly correlated with the degree of hepatic inflammation in patients with chronic liver disease, and its measurement has been proposed as a non-invasive index to evaluate this derangement (Marsillach J et al. Clin Biochem, 38, 2005, 1138-1140).

F. T Crews et al. proposed chronic ethanol treatment potentiates poly I:C blood and brain proinflammatory responses, which increases serum TNFα IL-1β, IL-6 and MCP-1 protein. These proteins in the blood enter the brain through transport systems or increase synthesis and secretion of cytokines into brain. Ethanol can also directly activate nuclear factor-kappa B (NF-κB) transcription of proinflammatory gene transcription within microglia and other cells. In brain, these proinflammatory cytokines activate microglia. Activated microglia amplify the brain neuroinflammatory response in at least three possible ways; a) microglial synthesis and release of cytokines that activate transcription factor NF-κB to synthesize and release more inflammatory cytokines, which further activates the microglia, producing more proinflammatory signals, b) involves activation of NADPH oxidase (NOX) in microglia that produces reactive oxygen species that activate transcription factor NF-κB to synthesize and release more inflammatory cytokines, c) involves HMGB1, a TLR activator, and TLR3 on microglia that stimulates NF-κB and microglial activation. HMGB1, an agonist that can activate multiple TLR receptors is released from cells by neurotransmitters including glutamate, proinflammatory cytokines and many other stimuli that amplify proinflammatory responses. F T Crews et. al. Journal of Neuroinflammation, 2012, 9, 130.

One or more parameters were selected to evaluate hangover related CNS symptoms. Some of these parameters are considered to be well correlated with hangover symptoms such as headache, cognitive deficit, impairment of memory etc, These are IL-12, CRP, HMGB1, MCP-1, IL-1beta, IL-10, WBC count (total & differential), serum acetate, acetylcholine esterase activity from brain homogenate, water maze experiment, rotarod test for motor coordination, spontaneous locomotor activity, etc.

One or more parameters were selected to evaluate alterations in liver functions, if any, we will estimate serum ALT, AST, ALP and TNF-α.

One or more parameters were selected to evaluate Veisalgia, if any, we will estimate serum: CRP, IL-12, (estimated in brain homogenate & plasma) & Acetyl choline esterase (brain memory) Worek F, et al., 2012, Determination of acetylcholinesterase activity by the Ellman assay: A versatile tool for in vitro research on medical countermeasures against organophosphate poisoning, Drug testing and analysis, 4:282-291, serum acetate, water maze experiment (Morris, R., 1984. Developments of a water-maze procedure for studying spatial learning in the rat. J. Neurosci. Methods 11, 47-60) or rotarod for subjective evaluation of brain coordination. (Karadayian A G and Cutrera R A, Alcohol hangover: type and time-extension of motor function impairments. Behav Brain Res. 2013, 15, 247, 165-173; Holloway F A, et al., 1993, Delayed Ethanol Effects on Physiological and Behavioral Indices in the Rat, Alcohol, 10, 511-519).

One or more parameters were selected to evaluate alterations in CNS functions, if any; we will estimate CRP, IL-12, (estimated in brain homogenate), HMGB1, MCP-1 (estimated in brain homogenate and plasma).

One or more parameters were selected to evaluate alterations in Immunological parameters, if any, we will estimate serum Immunology: IL-12, CRP, HMGB1, MCP-1, IL-1beta, IL-10, IL-17, IL-22, TNF-α.

One or more parameters will be selected to evaluate oxidative stress by measuring ROS parameter using a) ROS ELISA kit b) spectrophotometric assay of ROS (D-ROM test) c) Serum MDA by ELISA method d) Serum protein carbonyl content by ELISA method Serum/whole blood GSH and GSSG (Glutathione (GSSG/GSH), detection kit.

Materials and Methods

Animal Studies were Approved by Animal Ethics Committee (Reference No-PHARMA/327/IAEC; Dated 18 Mar. 2015).

Reagents

Distilled ethanol was obtained from Bengal Chemicals, West Bengal, India. Biochemical kits like AST, ALT, ALP and total protein were obtained from Span Diagnostics Ltd. Surat, India. Rat IL-12 ELISA kit (Elabscience Biotechnology Co. Ltd, WuHan, P.R.C.), Rat CRP ELISA kit (BD Biosciences, USA), Rat IFN-gamma ELISA kit (Biolegend, San Diego, Calif.) Rat MCP-1 ELISA kit (Elabscience Biotechnology Co. Ltd, WuHan, P.R.C.). All the chemicals used in the present study were of analytical grade and obtained from the following companies: Sigma (St. Louis, Mo., USA), Merck (Mumbai, India), S D fine chemicals (Mumbai, India) and Qualigen (Mumbai, India).

(1) Hangover Models in Rats (a) Animals

Male Wistar albino rats weighing 150-200 g were procured from local registered traders (CPCSEA Regd No. 1443/po/6/4/CPCSEA), Kolkata, India and were acclimatized for 7 days at standard housing condition (26° C.±2° C., 60-70% RH with 12±1 hours light and dark cycle).

Animals were fed with commercially available diet (Lipton India Pvt. Ltd, India) and water ad-libitum during the experiment period.

Experimental Design (b) Animal study model 1: Saline/Alcohol (4.0 gm/kg/day, p.o.)/Formulation with alcohol (4.0 gm/kg/day, p.o.) were administered (fed orally by orogastric cannula) for one day. 12-16 hours after the dose the animals were sacrificed and blood samples will be collected for estimation of biochemical parameters. Whole brain without cerebellum were dissected out, 10% homogenate was prepared with 0.1 M PB (pH 7.4). The homogenate solution was centrifuged at 10000 rpm for 20 minutes at 4° C. and the supernatant was used for estimation of acetylcholinesterase activity, which was estimated by Ellman's method (Ellman G L et al. A new and rapid colorimetric determination of acetylcholinesterase activity. Biochem Pharmacol, 1961, 7:88.)

(c) Animal study model 2: Saline/Alcohol (4.0 gm/kg/day, p.o.)/Formulation with alcohol (4.0 gm/kg/day, p.o.) were administered (fed orally by orogastric cannula) for 5 consecutive days. 12-16 hours after the last dose, the animals were sacrificed and blood samples were collected for estimation of biochemical parameters. Whole brain without cerebellum were dissected out, 10% homogenate was prepared with 0.1 M PB (pH 7.4). The homogenate solution was centrifuged at 10000 rpm for 20 minutes at 4° C. and the supernatant was used for estimation of acetylcholinesterase activity. To evaluate spatial learning and memory, the Morris water maze task was performed. In the water maze experiments, the rats were given one trial session each day for 5 consecutive days. During each trial, the time taken to swim to the platform (escape latency) was recorded. Next five days, rats were subjected to alcohol administration but without any swim training. On the $6^{th}$ day the rat was given swimming trial and escape latency period was recorded. The latency period of day 5 (before alcohol) was compared with post alcohol latency period (Vorhees C V and Williams M T. Morris water maze: procedures for assessing spatial and related forms of learning and memory, Nat Protoc, 2006, 1(2): 848-58.).

% Protection Calculated in Above Experiments:

% Protection=$1-[(T-NS)/(AL-NS)] \times 100$

T=Mean value of drug treated, NS=Mean value of normal control, AL=Mean value of alcohol alone.

EXAMPLES

Example 1

Hepatoprotection Study a) Model for Biological Testing:

Male Wistar albino rats weighing 150-200 g were procured and randomly divided into groups consisting of twelve (12) animals in each group. Hepatoprotection was induced by alcohol in rats by oral administration of 30% alcohol (4 gm/kg/day, p.o.) for 5 days and this group served as the negative control and treated groups received different formulation.

b) Preparation of Drug Solution:

All drug solutions were prepared in 40% aqueous alcohol, adjusting the pH in the range of 5.0-10.0 for evaluation of alcohol induced Hepatoprotection. This solution was further diluted with distilled water to obtain 30% aqueous alcoholic solution and administered orally by gavage to different rats group of step (a).

c) Evaluation of Hepato-Protective Activity:

On day 6, the animals were anaesthetized with ether and blood samples were collected by cardiac puncture and the serum was used for the assay of marker enzymes viz. serum alanine aminotransferase (ALT), aspartate aminotransferase (AST), alkaline phosphatase (ALP).

Example 2

Hangover and CNS Studies a) Model for Biological Testing:

Male Wistar albino rats weighing 150-200 g were procured and randomly divided into groups consisting of twelve (12) animals in each group. Alcohol induced hangover and CNS related biochemical changes and memory function in rats by oral administration of 30% alcohol (4 gm/kg/day, p.o.) for 1 and 5 days and this group served as the negative control and treated groups received different formulation.

b) Preparation of Drug Solution:

All drug solutions were prepared in 40% aqueous alcohol, adjusting the pH in the range of 5.0-10.0 for evaluation of alcohol induced hangover and CNS related biochemical parameters. This solution was further diluted with distilled water to obtain 30% aqueous alcoholic solution and administered orally by gavage to different rats group of step (a).

c) Evaluation of Hangover and CNS Parameters:

On day 2 and day 6, blood was collected from rats by cardiac puncture under mild ether anaesthesia and immediately after that the animals were decapitated and cerebral cortex was removed and stored at −20° C. for further use. Acetylcholine esterase from brain homogenate was estimated. Other parameters viz. interleukin-12 (IL-12) and Monocyte chemoattractant protein-1 (MCP-1) were also estimated from brain homogenate. Water maze was evaluated as per Morris water maze method as described in animal study model 2. For hangover, 1 day biochemical parameters were considered and for CNS, 5 days biochemical parameter were considered.

Example 3

Immunological Study a) Model for Biological Testing:

Male Wistar albino rats weighing 150-200 g were procured and randomly divided into groups consisting of twelve (12) animals in each group. Alcohol triggered modulation of the Immune response in rats by oral administration of 30% alcohol (4 gm/kg/day, p.o.) for 1 and 5 days and this group served as the negative control and treated groups received different formulation.

b) Preparation of Drug Solution:

All drug solutions were prepared in 40% aqueous alcohol, adjusting the pH in the range of 5.0-10.0 for evaluation of alcohol triggered modulation of the immune response. This solution was further diluted with distilled water to obtain 30% aqueous alcoholic solution and administered orally by gavage to different rats group of step (a).

c) Evaluation of Immunological Parameters:

On day 2 and day 6, the animals were anaesthetized with ether and blood samples were collected by cardiac puncture and the serum was used for the assay of marker enzymes viz. serum C-reactive protein (CRP), interleukin-12 (IL-12), Interferon gamma (IFN-$\gamma$) and Monocyte chemoattractant protein-1 (MCP-1). For hangover, 1 day immunology parameter were considered and for CNS, 5 days immunology parameter were considered.

Example 4

General Preparations/Formulations

Single Active Ingredient: Sugar Alcohol/Saponin Glycoside/Amino Acid Derivative (a) Sugar Alcohol (D-Mannitol or D-Xylitol or other) 0.5 g to 2.5 g was dissolved in aqueous alcohol (100 ml) to provide a corresponding 0.5% to 2.5% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Evaluation of—hepato-protective activities were carried out as per Example (1c), —hangover and CNS activities were carried out as per Example (2c) and —immunological activities were carried out as per Example (3c).

(b) Saponin Glycoside (18$\alpha$-GA or 18$\beta$-GA or $\alpha$-GA+$\beta$-GA or other) 0.04 g to 0.5 g was dissolved in aqueous alcohol (100 ml) to provide a corresponding 0.04% to 0.5% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Evaluation of—hepato-protective activities were carried out as per Example (1c), —hangover and CNS activities were carried out as per Example (2c) and —immunological activities were carried out as per Example (3c).

(c) Amino Acid Derivative (L-Alanyl-L-Glutamine or Oxidized L-Glutathione or hydrolyzed Casein Protein or other) 0.5 g to 3.0 g was dissolved in aqueous alcohol (100 ml) to provide a corresponding 0.5% to 3.0% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Evaluation of—hepato-protective activities were carried out as per Example (lc), —hangover and CNS activities were carried out as per Example (2c) and —immunological activities were carried out as per Example (3c).

Combination of Two Active Ingredients:

(d) Sugar Alcohol (D-Mannitol or D-Xylitol or other) 0.5 g to 2.5 g and Saponin Glycoside (18α-GA or 18β-GA or α-GA+β-GA or other) 0.04 g to 0.5 g were dissolved in aqueous alcohol (100 ml) to provide a corresponding 0.54% to 3.0% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Evaluation of—hepato-protective activities were carried out as per Example (lc), —hangover and CNS activities were carried out as per Example (2c) and —immunological activities were carried out as per Example (3c).

(e) Sugar Alcohol (D-Mannitol or D-Xylitol or other) 0.5 g to 2.5 g and Amino Acid Derivative (Alanyl-Glutamine or Oxidized Glutathione or hydrolyzed Casein Protein or other) 0.5 g to 3.0 g were dissolved in aqueous alcohol (100 ml) to provide a corresponding 1.0% to 5.5% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Evaluation of—hepato-protective activities were carried out as per Example (lc), —hangover and CNS activities were carried out as per Example (2c) and —immunological activities were carried out as per Example (3c).

(f) Amino Acid Derivative (Alanyl-Glutamine or Oxidized Glutathione or hydrolyzed Casein Protein or other) 0.5 g to 3.0 g and Saponin Glycoside (18α-GA or 18β-GA or α-GA+β-GA or other) 0.04 g to 0.5 g were dissolved in aqueous alcohol (100 ml) to provide a corresponding 0.54% to 3.5% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Evaluation of—hepato-protective activities were carried out as per Example (lc), —hangover and CNS activities were carried out as per Example (2c) and —immunological activities were carried out as per Example (3c).

Combination of Three Active Ingredients:

(g) Sugar Alcohol (D-Mannitol or D-Xylitol or other) 0.5 g to 2.5 g, Saponin Glycoside (18α-GA or 18β-GA or α-GA+β-GA or other) 0.04 g to 0.5 g and Amino Acid Derivative (Alanyl-Glutamine or Oxidized Glutathione or hydrolyzed Casein Protein or other) 0.5 g to 3.0 g were dissolved in aqueous alcohol (100 ml) to provide a corresponding 1.04% to 6.0% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Evaluation of—hepato-protective activities were carried out as per Example (lc), —hangover and CNS activities were carried out as per Example (2c) and —immunological activities were carried out as per Example (3c).

Two Active Ingredients+pH Adjusting Agent:

(h) As described in above in Example-4(d), (e) & (f), additionally comprising pH adjusting agent (such as potassium sorbate) in a range between 0.01 g to 0.2 g forming appropriate % of solution as shown below:
  Sugar Alcohol (0.5 g to 2.5 g)+Saponin Glycoside (0.04 g to 0.5 g)+pH Adjusting Agent (0.01 to 0.2 g) forming corresponding solution % of solution (0.55% to 3.2%).
  Sugar Alcohol (0.5 g to 2.5 g)+Amino Acid Derivative (0.5 g to 3.0 g)+pH Adjusting Agent (0.01 to 0.2 g) forming corresponding solution % of solution (1.01% to 5.7%).
  Amino Acid Derivative (0.5 g to 3.0 g)+Saponin Glycoside (0.04 g to 0.5 g)+pH Adjusting Agent (0.01 to 0.2 g) forming corresponding solution % of solution (0.55% to 3.7%).

Three Active Ingredients+pH Adjusting Agent:

(i) As described in above in Example-4(g), additionally comprising pH adjusting agent (such as potassium sorbate) in a range between 0.01 g to 0.2 g forming appropriate % of solution as shown below:
  Sugar Alcohol (0.5 g to 2.5 g)+Saponin Glycoside (0.04 g to 0.5 g)+Amino Acid Derivative (0.5 g to 3.0 g)+pH Adjusting Agent (0.01 to 0.2 g) forming corresponding solution % of solution (1.05% to 6.2%).

Three Active Ingredients+pH Adjusting Agent+Flavouring Agent:

(j) As described in above in Example-4(i) additionally comprising flavouring agent in a range of 0.01 g to 0.2 g forming appropriate % of solution as shown below:
  Sugar Alcohol (0.5 g to 2.5 g)+Saponin Glycoside (0.04 g to 0.5 g)+Amino Acid Derivative (0.5 g to 3.0 g)+pH Adjusting Agent (0.01 to 0.2 g)+flavouring agent (0.01 g to 0.2 g) forming corresponding solution % of solution (1.06% to 6.4%).

Preparations/formulations comprising a single ingredient, two ingredients, two ingredients+pH adjusting Agent, three ingredients, three ingredients+pH adjusting Agent and three ingredients+pH adjusting Agent+flavouring Agent as mentioned in the Tables 1-4 can be prepared by the way as described in above examples 1-4. Further non-limiting specific examples are as given below. The examples below are illustrative and in similar way other combinations and/or beverage comprising combinations of active ingredients can be prepared by taking suitable amounts of active ingredients and optionally suitable amounts of pH adjusting agents and/or flavouring agents.

Example 5

D-Mannitol (0.5 g) was dissolved in aqueous alcohol (100 ml) to provide 0.5% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Evaluation of—hepato-protective activities were carried out as per Example (lc), —hangover and CNS activities were carried out as per Example (2c) and —immunological activities were carried out as per Example (3c).

Example 6

D-Mannitol (2.5 g) was dissolved in aqueous alcohol (100 ml) to provide 2.5% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

Example 7

β-GA (0.1 g) was dissolved in aqueous alcohol (100 ml) to provide 0.1% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

Example 8

Dipeptide (L-Ala-L-Gln) (1.0 g) was dissolved in aqueous alcohol (100 ml) to provide 1.0% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

Example 9

Oligopeptide (Oxidized L-Glutathione) (2.0 g) was dissolved in aqueous alcohol (100 ml) to provide 2.0% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

Example 10

β-GA (0.1 g)+D-Mannitol (1.2 g) was dissolved in aqueous alcohol (100 ml) to provide 1.3% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

Example 11

D-Mannitol (1.2 g)+L-Ala-L-Gln (1.0 g) was dissolved in aqueous alcohol (100 ml) to provide 2.2% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

Example 12

β-GA (0.1 g)+L-Ala-L-Gln (1.0 g) was dissolved in aqueous alcohol (100 ml) to provide 1.1% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

Example 13

D-Mannitol (1.2 g)+L-Ala-L-Gln (1.25 g) was dissolved in aqueous alcohol (100 ml) to provide 2.45% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

Example 14

β-GA (0.1 g)+L-Ala-L-Gln (1.25 g) was dissolved in aqueous alcohol (100 ml) to provide 1.35% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

Example 15

β-GA (0.1 g)+D-Mannitol (1.2 g)+L-Ala-L-Gln (1.0 g) was dissolved in aqueous alcohol (100 ml) to provide 2.3% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

Example 16

β-GA (0.04 g)+D-Mannitol (0.5 g)+L-Ala-L-Gln (0.5 g) was dissolved in aqueous alcohol (100 ml) to provide 1.04% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

Example 17

β-GA (0.1 g)+D-Mannitol (1.2 g)+L-Ala-L-Gln (0.5 g) was dissolved in aqueous alcohol (100 ml) to provide 1.8% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

Example 18

β-GA (0.1 g)+D-Mannitol (1.2 g)+L-Ala-L-Gln (1.25 g) was dissolved in aqueous alcohol (100 ml) to provide 2.55% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

Example 19

β-GA (0.1 g)+D-Mannitol (1.2 g)+L-Ala-L-Gln (1.5%) was dissolved in aqueous alcohol (100 ml) to provide 2.8% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

Example 20

β-GA (0.1 g)+D-Mannitol (1.2 g)+L-Ala-L-Gln (1.0 g)+Potassium Sorbate (0.1 g) was dissolved in aqueous alcohol (100 ml) to provide 2.4% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

Example 21

β-GA (0.1 g)+D-Mannitol (1.2 g)+Oxidised Glutathione (2.0 g) was dissolved in aqueous alcohol (100 ml) to provide 3.3% solution. This solution was administered in several portions to one of the rats group of Example (1a) or (2a) or (3a). The administration was carried out over as per example 1(a) or 2(a) or 3(a); each day 10 ml sample was diluted with 6 ml distilled water to make 25% aqueous alcoholic solution (16 ml) and fed orally (10 ml/kg/day). Different activities were evaluated in similar ways as carried out in Example 5 above.

The comparative tests results of any single active ingredient, any two active ingredients and all the three active ingredients comprising different combinations at different amounts show increased protection (%) and synergism (%) of various test parameters in case of all the three active ingredients each at appropriate amount are depicted in below tables 1-4.

Results and Discussions:

TABLE 1

STUDY: HEPATOPROTECTIVE

| S. No. | 5 days | ALT Pro | ALT Syn | AST Pro | AST Syn | ALP Pro | ALP Syn |
|---|---|---|---|---|---|---|---|
|  | Normal | 100 |  | 100 |  | 100 |  |
|  | Alcohol | 0 |  | 0 |  | 0 |  |
| 1 | 0.04 GA + 1.2Xyl + 1DP | 44.23 | 10.99 | 46.39 | 0.30 | 52.18 | −2.14 |
| 2 | 1.2Xyl + 1 DP | 38.96 |  | 44.07 |  | 50.54 |  |
| 3 | 0.04 GA + 1.2Man + 1DP | 46.02 | 13.02 | 50.98 | 11.02 | 53.25 | 1.93 |
| 4 | 1.2Man + 1 DP | 39.83 | 8.85 | 43.74 | 16.08 | 49.46 | 13.86 |
| 5 | 0.04 GA + 2.5Man + 1DP | 54.86 | 23.98 | 63.34 | 0.49 | 64.66 | 16.50 |
| 6 | 2.5Man + 1 DP | 43.36 | −16.29 | 60.85 | 4.46 | 52.72 | −1.84 |
| 7 | 0.04aGA + 1.2Man + 1DP | 42.49 | −3.98 | 46.39 | −26.40 | 50 | −9.91 |
| 8 | 0.04 GA + 1.2Man | 22.12 | −8.14 | 26.65 | 10.22 | 27.43 | 0.62 |
| 9 | 0.1 GA + 1.2Man + 1DP | 47.8 | 17.07 | 61.83 | 34.62 | 57.07 | 14.76 |
| 10 | 0.04GA + 0.5 Ma + 0.5 DP | 22.4 | 45.55 | 34 | 140.79 | 30.68 | 80.79 |
| 11 | 0.1 GA + 1 DP | 18.39 | 4.25 | 21.14 | −11.66 | 31.66 | 25.39 |
| 12 | 1.2 Man | 23.19 |  | 22 |  | 24.48 |  |
| 13 | 0.1 GA | 4.24 |  | 8.25 |  | 6.29 |  |
| 14 | 0.15 GA + 1.2 Man + 1.0 DP | 54.41 | 13.85 | 64.86 | 33.43 | 58.05 | 4.29 |
| 15 | 0.15GA + 1.2 Man | 34.39 |  | 32.93 |  | 36.7 |  |
| 16 | 0.1 GA + 2.5 Man + 1.0 DP | 64.02 | 14.24 | 68.58 | 3.13 | 65.05 | 8.42 |
| 17 | 2.5 Man | 38.4 |  | 42.57 |  | 34.75 |  |
| 18 | 0.1GA + 1.2M + 1.25DP | 51.19 | 13.71 | 64.57 | 23.58 | 58.45 | 9.25 |
| 19 | 1.25 DP | 17.59 |  | 22 |  | 22.73 |  |
| 20 | 0.1 GA + 1.25 DP | 29.59 | 35.55 | 30.28 | 0.10 | 30.91 | 6.51 |
| 21 | 0.1 GA + 1.2 Man + 2.0 DP | 59.39 | −10.37 | 66.01 | 8.27 | 70.79 | 19.07 |

TABLE 1-continued

STUDY: HEPATOPROTECTIVE

| S. No. | 5 days | ALT Pro | ALT Syn | AST Pro | AST Syn | ALP Pro | ALP Syn |
|---|---|---|---|---|---|---|---|
| 22 | 0.1 GA + 1.2 Man + 1.5 DP | 53.51 | 27.07 | 64.06 | 26.85 | 69.86 | 31.51 |
| 23 | 2.0 DP | 38.83 | | 30.72 | | 28.68 | |
| 24 | 1.5 DP | 14.68 | | 20.25 | | 22.35 | |
| 25 | 0.1 GA + 1.2 Man + 0.75 DP | 34.11 | 4.28 | 45.11 | 14.52 | 52.48 | 22.02 |
| 26 | 0.75 DP | 5.28 | | 9.14 | | 12.24 | |
| 27 | 0.1 GA + 1.2 Man + 0.1 KS | 28.51 | 3.94 | 31.1 | 2.81 | 34.64 | 12.58 |
| 28 | 1 DP | 13.4 | | 15.68 | | 18.96 | |
| 29 | 0.1 GA + 1.2 Man + 1 DP + 0.1 KS | 66.51 | 58.70 | 60.8 | 29.97 | 74.13 | 38.30 |
| 30 | 0.1 GA + 1.2 Man − 0.1 KS | 29.06 | 5.94 | 26.33 | −12.96 | 33.51 | 8.90 |
| 31 | 0.1 GA + 1.2 Man + 0.5 DP | 49.7 | 35.94 | 45.56 | 26.17 | 49.94 | 32.40 |
| 32 | 0.1 GA + 1.2 Man + 3.0 DP | 67.42 | 18.01 | 57.01 | −9.79 | 66.03 | 10.33 |
| 33 | 0.5 DP | 9.13 | | 5.86 | | 6.95 | |
| 34 | 3 DP | 29.7 | | 32.95 | | 29.08 | |
| 35 | 0.04 GA | 0.89 | | 2.18 | | 2.78 | |
| 36 | 0.04GA + 0.5 Ma | 6.26 | 39.73 | 8.26 | 27.86 | 10.02 | 32.54 |
| 37 | 0.1 KS | 0.11 | | 0.09 | | 0 | |
| 38 | 0.3 GA | 25.62 | | 20.46 | | 11.68 | |
| 39 | 0.3 GA + 1.2 M + 1 DP | 63.55 | 2.15 | 59.04 | 1.55 | 47.5 | −13.82 |
| 40 | 0.1 GA + 1.2 M + 1 G | 36.95 | −24.22 | 49.21 | 39.05 | 27.05 | −34.34 |
| 41 | 0.1 GA + 1.2 M + 2 G | 83.25 | 24.27 | 75.2 | 72.28 | 35.65 | −19.33 |
| 42 | 2G | 37.93 | | 17.32 | | 10.68 | |
| 43 | 1G | 19.7 | | 9.06 | | 7.69 | |
| 44 | 0.1 GA + 1.2 M + 1 CP | 30.54 | −20.51 | 30.32 | −22.87 | 30.04 | −33.67 |
| 45 | 0.1 GA + 1.2 M + 2 CP | 48.76 | −9.17 | 53.94 | 20.32 | 36.13 | −31.40 |
| 46 | 2CP | 24.62 | | 18.5 | | 19.16 | |
| 47 | 1CP | 9.36 | | 12.98 | | 11.78 | |
| 48 | 1.2 Man + 1.25 DP | 37.93 | −6.99 | 36.62 | −16.77 | 37.82 | −19.89 |
| 49 | 0.5 Man | 3.59 | | 4.28 | | 4.78 | |
| 50 | 0.1 GA + 1.2 Man + 3G | 60.13 | 2.89 | 61.95 | 11.96 | 40.51 | −13.54 |
| 51 | 3G | 31.01 | | 25.08 | | 16.09 | |
| 52 | 0.1 GA + 1.2 Man + 2.5 G | 69.61 | 16.58 | 53.71 | 0.65 | 36.42 | −18.59 |
| 53 | 0.1 GA + 1.2 Man + 1.5 G | 51.27 | −1.63 | 42.73 | −5.31 | 28.69 | −26.08 |
| 54 | 0.3 GA + 1.2 Man + 2G | 55.70 | −35.79 | 52.15 | −12.76 | 47.79 | 2.04 |
| 55 | 0.04 GA + 0.5 Man + 2G | 31.63 | −25.42 | 23.34 | −1.83 | 16.85 | −7.63 |
| 56 | 1.5 G | 24.69 | | 14.88 | | 8.04 | |
| 57 | 0.1 GA + 2.5 Man + 0.5 G | 44.30 | −11.81 | 42.73 | −25.15 | 45.37 | −3.99 |
| 58 | 2.5 G | 32.28 | | 23.12 | | 13.96 | |
| 59 | 0.5 G | 7.59 | | 6.27 | | 6.22 | |
| 60 | 0.04a GA | 1.26 | | 2.24 | | 1.08 | |
| 61 | 0.04 aGA + 1.2Man | 24.06 | −1.60 | 21.95 | −9.45 | 25.06 | −1.96 |

For all tables (1-4) 50

Pro: Protection (%) and Syn: Synergism (%)

Ingredients:— Man: D-Mannitol; Xyl: D-Xylitol; aGA: 18α-GA; GA: 18β-GA; DP: Dipeptide (L-Ala-L-Gln); CP: Hydrolysed Casein Protein; G: Oxidised Glutathione; KS: Potassium Sorbate. Amounts of ingredients are in mass concentration (%).

TABLE 2

STUDY: CNS AND IMMUNOLOGY

STUDY PARAMETERS

| S. No. | 5 Day | ACHe Pro | ACHe Syn | CRP Pro | CRP Syn | IL12 Pro | IL12 Syn | MCP-1 Pro | MCP-1 Syn | IFN-Gamma Pro | IFN-Gamma Syn | Brain IL12 Pro | Brain IL12 Syn | Brain MCP-1 Pro | Brain MCP-1 Syn |
|---|---|---|---|---|---|---|---|---|---|---|---|---|---|---|---|
| | Normal Alcohol | 100 0 | | 100 0 | | 100 0 | | 100 0 | | 100 0 | | 100.00 0.00 | | 100 0 | |
| 1 | 0.04 GA + 1.2Xyl + 1DP | 57.24 | 11.84 | 41.3 | 15.65 | 38.98 | 4.42 | 17.59 | −17.03 | 17.35 | 6.18 | 30.10 | 8.46 | 22.52 | 2.13 |
| 2 | 1.2Xyl + 1 DP | 49.75 | | 33.34 | | 34.25 | −2.38 | 17.82 | −14.71 | 15.27 | | 26.47 | | 20.47 | |
| 3 | 0.04 GA + 1.2Man + 1DP | 60.65 | 10.41 | 42.05 | 2.54 | 44.8 | | 18.27 | | 19.68 | 15.02 | 32.31 | 2.03 | 24.11 | 2.03 |
| 4 | 1.2Man + 1 DP | 53.5 | 148.95 | 38.64 | 73.66 | 42.81 | 24.59 | 18.04 | 22.72 | 16.04 | 3.97 | 30.39 | 25.47 | 22.05 | −13.73 |
| 5 | 0.04 GA + 2.5Man + 1DP | 71.21 | 11.65 | 43.18 | 30.65 | 57.33 | 5.58 | 31.57 | 33.32 | 36.54 | 14.62 | 42.17 | 21.71 | 36.58 | 11.42 |
| 6 | 2.5Man + 1 DP | 62.35 | 80.62 | 30.68 | 9.07 | 51.22 | 5.76 | 20.3 | −51.69 | 30.81 | 28.66 | 33.36 | −13.63 | 31.25 | −13.03 |
| 7 | 0.04aGA + 1.2Man + 1DP | 60.65 | −4.91 | 28.05 | −15.13 | 40.51 | −25.40 | 17.59 | −25.72 | 19.15 | −39.93 | 27.84 | −19.64 | 25.21 | −23.21 |
| 8 | 0.04 GA + 1.2Man | 18.74 | −1.42 | 16.3 | −10.88 | 22.02 | 4.86 | 0 | −100.00 | 9.83 | 29.17 | 13.40 | −11.88 | 15.26 | −3.78 |
| 9 | 0.1 GA + 1.2Man + 1DP | 64.4 | 108.48 | 46.98 | 71.21 | 56.88 | 41.46 | 22.78 | 54.97 | 28.76 | 86.42 | 38.79 | 39.18 | 28.53 | −2.09 |
| 10 | 0.04GA + 0.5 Ma + 0.5 DP | 19.4 | 53.97 | 14.18 | −13.43 | 10.32 | −16.23 | 14.53 | 28.02 | 18.75 | 201.65 | 13.81 | 40.95 | 16.21 | 56.62 |
| 11 | 0.1 GA + 1 DP | 22.73 | 70.77 | 16.25 | 41.06 | 20.42 | −8.39 | 11.05 | 54.76 | 12.51 | 40.76 | 15.49 | 11.04 | 14.25 | −4.10 |
| 12 | 1.2 Man | 17.58 | | 15.92 | | 17.92 | | 7.56 | | 6.54 | | 13.92 | | 14.28 | |
| 13 | 0.1 GA | 9.4 | | 5.19 | | 5.85 | | 0 | | 0 | | 3.66 | | 3.58 | |
| 14 | 0.15GA + 1.2Man + 1.0 DP | 60.61 | 58.87 | 42.91 | 58.40 | 58.61 | 45.04 | 26.16 | 11.70 | 25.02 | 15.47 | 40.23 | 34.28 | 33.25 | 14.93 |
| 15 | 0.15GA + 1.2 Man | 34.24 | | 20.76 | | 23.97 | | 16.28 | | 12.78 | | 19.67 | | 17.65 | |
| 16 | 0.1GA + 2.5 Man + 1.0 DP | 69.09 | 57.31 | 51.9 | 55.76 | 62.39 | 14.94 | 45.35 | 7.92 | 44.61 | 86.28 | 52.73 | 24.71 | 51.29 | 29.82 |
| 17 | 2.5 Man | 30.61 | | 21.8 | | 31.99 | | 34.88 | | 15.06 | | 28.33 | | 24.65 | |
| 18 | 0.1GA + 1.2M + 1.25DP | 62.73 | 71.02 | 43.24 | 19.02 | 56.76 | 22.12 | 33.14 | 111.08 | 29.82 | 51.91 | 41.71 | 24.88 | 33.68 | −3.96 |
| 19 | 1.25 DP | 9.7 | | 15.22 | | 22.71 | | 8.14 | | 13.09 | | 15.82 | | 17.21 | |
| 20 | 0.1 GA + 1.25 DP | 19.7 | 3.14 | 18 | −11.81 | 25.35 | −11.24 | 15.7 | 92.87 | 14.79 | 12.99 | 19.41 | −0.35 | 18.58 | −10.63 |
| 21 | 0.1GA + 1.2 Man + 2.0DP | 69.12 | 8.29 | 71.59 | 48.07 | 65.23 | 22.36 | 31.83 | 19.12 | 47.12 | 59.98 | 56.13 | 31.60 | 55.86 | 32.31 |
| 22 | 0.1GA + 1.2 Man + 1.5 DP | 63.92 | 51.22 | 67.87 | 105.17 | 59.66 | 28.86 | 28.05 | 51.05 | 39.68 | 104.96 | 46.46 | 38.63 | 30.24 | −16.21 |
| 23 | 2.0 DP | 36.85 | | 27.24 | | 29.54 | | 19.16 | | 22.91 | | 25.08 | | 24.36 | |
| 24 | 1.5 DP | 15.29 | | 11.97 | | 22.53 | | 11.01 | | 12.82 | | 15.94 | | 18.23 | |
| 25 | 0.1GA + 1.2 Man + 0.75DP | 39.3 | 16.58 | 34.8 | 39.82 | 46.3 | 22.97 | 7.39 | −11.07 | 28.17 | 131.61 | 26.76 | 8.86 | 18.56 | −32.48 |
| 26 | 0.75 DP | 6.73 | | 3.78 | | 13.88 | | 0.75 | | 5.62 | | 7.01 | | 9.63 | |
| 27 | 0.1 GA + 1.2 Man + 0.1 KS | 24.56 | −8.97 | 28.47 | 34.86 | 25 | 5.17 | 6.16 | −18.52 | 19.37 | 196.23 | 18.97 | 7.95 | 16.26 | −8.96 |
| 28 | 1 DP | 3.91 | | 6.33 | | 16.44 | | 7.14 | | 8.89 | | 10.30 | | 11.28 | |
| 29 | 0.1 GA + 1.2 Man + 1 DP + 0.1 KS | 59.35 | 108.47 | 71.18 | 104.54 | 60.78 | 46.67 | 21.18 | 59.25 | 44.94 | 59.02 | 47.50 | 62.27 | 36.85 | 33.81 |
| 30 | 0.1 GA + 1.2 Man − 0.1 KS | 21.95 | −18.64 | 25.66 | 21.55 | 21.56 | −9.30 | 4.06 | −46.30 | 17.60 | 169.15 | 16.79 | −4.50 | 15.86 | −11.20 |

TABLE 2-continued

STUDY: CNS AND IMMUNOLOGY

STUDY PARAMETERS

| S. No. | 5 Day | ACHe Pro | ACHe Syn | CRP Pro | CRP Syn | IL12 Pro | IL12 Syn | MCP-1 Pro | MCP-1 Syn | IFN-Gamma Pro | IFN-Gamma Syn | Brain IL12 Pro | Brain IL12 Syn | Brain MCP-1 Pro | Brain MCP-1 Syn |
|---|---|---|---|---|---|---|---|---|---|---|---|---|---|---|---|
| 31 | 0.1 GA + 1.2 Man + 0.5 DP | 48.62 | 55.29 | 53.97 | 98.13 | 34.8 | 31.77 | 9.01 | 17.62 | 25.14 | 155.08 | 29.59 | 48.53 | 20.58 | -10.44 |
| 32 | 0.1 GA + 1.2 Man + 3.0 DP | 77.56 | -10.05 | 73.68 | 51.29 | 63 | 11.76 | 18.47 | -12.34 | 52.28 | 42.14 | 53.38 | 18.24 | 58.36 | 7.20 |
| 33 | 0.5 DP | 4.33 | | 6.13 | | 2.64 | | 0.1 | | 3.32 | | 2.35 | | 5.12 | |
| 34 | 3 DP | 59.25 | | 27.59 | | 32.6 | | 13.51 | | 30.24 | | 27.57 | | 36.58 | |
| 35 | 0.04 GA | 1.43 | | 2.37 | | 3.08 | | 3.38 | | 1.07 | | 1.28 | | 1.58 | |
| 36 | 0.04GA + 0.5 Ma | 8.27 | 24.36 | 10.25 | 30.91 | 9.68 | 18.63 | 11.25 | 29.76 | 2.9 | 9.43 | 7.45 | 20.16 | 5.23 | 20.79 |
| 37 | 0.1 KS | 0 | | 0.87 | | 1.2 | | 1.04 | | 0 | | 0.00 | 0 | 0 | 0 |
| 38 | 0.3 GA | 21.5 | | 15.63 | | 10.07 | | 15.46 | | 23.18 | | 15.63 | | 21.36 | |
| 39 | 0.3 GA + 1.2 M + 1 DP | 63.52 | 47.76 | 48.75 | 28.70 | 49.39 | 11.16 | 33.8 | 12.07 | 36.11 | -6.47 | 44.05 | 10.55 | 44.26 | -5.67 |
| 40 | 0.1 GA + 1.2 M + 1 G | 34.53 | 3.54 | 33.75 | -0.12 | 24.49 | 13.59 | 17.76 | 71.43 | 29.14 | 0.96 | 22.47 | -15.06 | 25.36 | -9.01 |
| 41 | 0.1 GA + 1.2 M + 2 G | 67.43 | 46.40 | 56.88 | 18.11 | 54.06 | 19.13 | 43.55 | 165.87 | 48.03 | 9.73 | 52.44 | 37.92 | 55.28 | 31.09 |
| 42 | 2G | 24.11 | | 22.5 | | 23.82 | | 12.32 | | 26.17 | | 21.24 | | 26.31 | |
| 43 | 1G | 11.4 | | 8.13 | | 0 | | 6.3 | | 11.26 | | 9.67 | | 12.01 | |
| 44 | 0.1 GA + 1.2 M + 1 CP | 37.14 | 2.37 | 22.5 | -25.10 | 11.02 | -61.54 | 18.91 | 11.56 | 31.47 | -4.15 | 18.75 | -27.08 | 22.58 | -17.08 |
| 45 | 0.1 GA + 1.2 M + 2 CP | 60.59 | 13.15 | 52.5 | 19.89 | 31.84 | -3.92 | 30.66 | 18.65 | 56.29 | 7.46 | 40.90 | 16.77 | 48.59 | 30.20 |
| 46 | 2CP | 31.6 | | 18.13 | | 11.58 | | 21.78 | | 34.78 | | 18.24 | | 21.46 | |
| 47 | 1CP | 14.33 | | 4.38 | | 7.09 | | 12.89 | | 15.23 | | 8.93 | | 11.37 | |
| 48 | 1.2 Man + 1.25 DP | 54.07 | 98.20 | 41.25 | 32.47 | 41.78 | 2.83 | 23.78 | 51.46 | 25.51 | 29.95 | 33.01 | 10.98 | 25.21 | -19.94 |
| 49 | 0.5 Man | 5.22 | | 5.46 | | 5.08 | | 5.29 | | 1.58 | | 4.92 | | 2.75 | |
| 50 | 0.1 GA + 1.2 Man + 3G | 72.76 | 32.05 | 62.82 | 30.79 | 57.92 | 8.86 | 49.60 | 108.09 | 54.23 | 48.15 | 55.96 | 32.72 | 60.14 | 25.37 |
| 51 | 3G | 28.12 | | 26.92 | | 29.43 | | 16.28 | | 30.06 | | 24.59 | | 30.11 | |
| 52 | 0.1 GA + 1.2 Man + 2.5 G | 68.70 | 24.69 | 60.26 | 25.45 | 55.85 | 8.53 | 45.64 | 105.15 | 52.24 | 50.77 | 54.68 | 28.40 | 57.36 | 66.79 |
| 53 | 0.1 GA + 1.2 Man + 1.5 G | 49.28 | 17.18 | 46.15 | 36.02 | 46.05 | 58.01 | 31.36 | 67.89 | 36.54 | 68.31 | 35.16 | 7.24 | 37.14 | 9.85 |
| 54 | 0.3 GA + 1.2 Man + 2G | 69.86 | 10.55 | 61.54 | 13.85 | 55.22 | 6.59 | 50.40 | 42.61 | 57.60 | 3.06 | 57.69 | 13.59 | 61.25 | -1.13 |
| 55 | 0.04 GA + 0.5 Man + 2G | 40.87 | 32.87 | 30.77 | 1.45 | 31.16 | -2.56 | 25.40 | 21.01 | 37.92 | 31.57 | 32.43 | 18.20 | 39.36 | 28.46 |
| 56 | 1.5 G | 15.07 | | 12.82 | | 5.37 | | 11.12 | | 15.17 | | 15.21 | | 15.95 | |
| 57 | 0.1 GA + 2.5 Man + 0.5G | 39.71 | -14.87 | 38.46 | 15.15 | 40.83 | 3.98 | 37.70 | -5.84 | 23.05 | 7.07 | 37.14 | 1.74 | 36.85 | 11.97 |
| 58 | 2.5 G | 28.12 | | 26.92 | | 27.69 | | 14.69 | | 28.11 | | 25.01 | | 16.53 | |
| 59 | 0.5 G | 6.64 | | 6.41 | | 1.42 | | 5.16 | | 6.47 | | 4.52 | | 4.68 | |
| 60 | 0.04a GA | 0.1 | | 0.1 | | 0.1 | | 0.1 | | 0.1 | | 0.1 | | 0.1 | |
| 61 | 0.04 aGA + 1.2Man | 20.59 | 16.46 | 9.25 | -42.26 | 14.62 | -18.87 | 12.58 | 64.23 | 9.24 | 39.16 | 11.26 | -19.69 | 19.89 | 38.32 |

TABLE 3

STUDY: HANGOVER

| S. No. | 1 Day | ACHe Pro | ACHe Syn | CRP Pro | CRP Syn | IL12 Pro | IL12 Syn | MCP-1 Pro |
|---|---|---|---|---|---|---|---|---|
| | Normal | 100 | | 100 | | 100 | | 100 |
| | Alcohol | 0 | | 0 | | 0 | | 0 |
| 1 | 0.04 GA + 1.2Xyl + 1DP | 67.32 | 6.77 | 27.58 | −2.65 | 13.51 | −3.15 | 12.38 |
| 2 | 1.2Xyl + 1 DP | 62.46 | | 26.29 | | 12.9 | | 9.28 |
| 3 | 0.04 GA + 1.2Man + 1DP | 69.02 | 3.87 | 29.5 | 10.36 | 14.7 | −0.34 | 16.14 |
| 4 | 1.2Man + 1 DP | 65.86 | 59.47 | 24.69 | −38.24 | 13.7 | −30.03 | 6.41 |
| 5 | 0.04 GA + 2.5Man + 1DP | 72.66 | 4.76 | 43.6 | 80.46 | 15.89 | 12.22 | 5.08 |
| 6 | 2.5Man + 1 DP | 68.77 | 6.00 | 22.12 | −55.43 | 13.11 | −52.38 | 5.47 |
| 7 | 0.04aGA + 1.2Man + 1DP | 62.7 | −9.60 | 26.62 | 10.18 | 12.51 | −11.65 | 8.4 |
| 8 | 0.04 GA + 1.2Man | 30.13 | 36.15 | 13.46 | 25.56 | 3.78 | −73.93 | 1.58 |
| 9 | 0.1 GA + 1.2Man + 1DP | 75.34 | 41.91 | 39.42 | −12.65 | 14.49 | −34.67 | 19.89 |
| 10 | 0.04GA + 0.5 Ma + 0.5 DP | 28.86 | 209.32 | 10.94 | −1.00 | 15.36 | 171.38 | 20.85 |
| 11 | 0.1 GA + 1 DP | 26.42 | −16.26 | 7.72 | −78.82 | 8.51 | −2.52 | 10.43 |
| 12 | 1.2 Man | 21.54 | | 8.68 | | 13.45 | | 11.85 |
| 13 | 0.1 GA | 11.79 | | 5.15 | | 2.6 | | 3.79 |
| 14 | 0.15 GA + 1.2 Man + 1.0 DP | 64.23 | 5.64 | 40.84 | −24.10 | 18.39 | −3.31 | 33.65 |
| 15 | 0.15GA + 1.2 Man | 41.04 | | 22.51 | | 12.89 | | 18.96 |
| 16 | 0.1 GA + 2.5 Man + 1.0 DP | 75.61 | −1.38 | 55.94 | 2.12 | 35.8 | 18.82 | 40.76 |
| 17 | 2.5 Man | 45.12 | | 18.33 | | 21.4 | | 22.75 |
| 18 | 0.1GA + 1.2M + 1.25DP | 69.1 | 28.77 | 49.52 | 102.62 | 31.82 | 2.65 | 20.38 |
| 19 | 1.25 DP | 20.33 | | 10.61 | | 14.95 | | 14.22 |
| 20 | 0.1 GA + 1.25 DP | 29.27 | −8.87 | 13.5 | −14.34 | 17.56 | 0.06 | 22.75 |
| 21 | 0.1 GA + 1.2 Man + 2.0 DP | 62.55 | −3.95 | 52.9 | 12.63 | 42.86 | −10.62 | 33.55 |
| 22 | 0.1 GA + 1.2 Man + 1.5 DP | 60.31 | 10.72 | 42.7 | 6.86 | 28.85 | −20.22 | 24.46 |
| 23 | 2.0 DP | 31.79 | | 33.14 | | 31.9 | | 21.43 |
| 24 | 1.5 DP | 21.14 | | 26.13 | | 20.11 | | 11.04 |
| 25 | 0.1 GA + 1.2 Man + 0.75 DP | 44.16 | 4.47 | 36.06 | 21.17 | 17.06 | −44.77 | 8.01 |
| 26 | 0.75 DP | 8.94 | | 15.93 | | 14.84 | | 5.25 |
| 27 | 0.1 GA + 1.2 Man + 0.1 KS | 34.71 | 4.14 | 34.59 | 150.11 | 0 | −100.00 | 4.91 |
| 28 | 1 DP | 19.76 | | 31.3 | | 6.13 | | 20.74 |
| 29 | 0.1 GA + 1.2 Man + 1 DP + 0.1 KS | 78.62 | 44.34 | 28.78 | −56.32 | 11.2 | 82.71 | 22.7 |
| 30 | 0.1 GA + 1.2 Man − 0.1 KS | 32.64 | −2.07 | 35.07 | 153.58 | 33.51 | 108.79 | 21.95 |
| 31 | 0.1 GA + 1.2 Man + 0.5 DP | 48.62 | 29.10 | 28.97 | 62.02 | 13.04 | −21.40 | 16.58 |
| 32 | 0.1 GA + 1.2 Man + 3.0 DP | 77.56 | −16.22 | 60.49 | 8.70 | 36.41 | −22.58 | 35.88 |
| 33 | 0.5 DP | 4.33 | | 4.05 | | 0.54 | | 4.33 |
| 34 | 3 DP | 59.25 | | 41.82 | | 30.98 | | 29.69 |
| 35 | 0.04 GA | 0.59 | | 2.04 | | 1.05 | | 0.6 |
| 36 | 0.04GA + 0.5 Ma | 5 | 6.16 | 7.00 | −6.91 | 5.12 | 10.34 | 4.25 |
| 37 | 0.1 KS | 0.24 | | 1.2 | | 0.89 | | 0.16 |
| 38 | 0.3 GA | 17.19 | | 11.21 | | 7.48 | | 13.97 |
| 39 | 0.3 GA + 1.2 M + 1 DP | 61.4 | 4.98 | 44.86 | −12.37 | 19.83 | −26.72 | 38.72 |
| 40 | 0.1 GA + 1.2 M + 1 G | 33.68 | −23.23 | 24.3 | −42.25 | 19.12 | −51.84 | 22.55 |
| 41 | 0.1 GA + 1.2 M + 2 G | 74.39 | 19.77 | 57.94 | 10.66 | 32.19 | −32.78 | 57.11 |
| 42 | 2G | 29.47 | | 17.29 | | 14.38 | | 21.32 |
| 43 | 1G | 11.23 | | 7.01 | | 6.19 | | 10.54 |
| 44 | 0.1 GA + 1.2 M + 1 CP | 41.75 | −0.60 | 19.16 | −60.12 | 15.67 | −65.40 | 23.52 |
| 45 | 0.1 GA + 1.2 M + 2 CP | 64.21 | 6.38 | 50.47 | −20.61 | 35.64 | −28.98 | 37.75 |
| 46 | 2CP | 27.72 | | 28.5 | | 16.67 | | 23.03 |
| 47 | 1CP | 9.36 | | 12.98 | | 11.78 | | 14.33 |
| 48 | 1.2 Man + 1.25 DP | 55.09 | 31.57 | 27.1 | 40.49 | 15.52 | −45.35 | 12.99 |
| 49 | 0.5 Man | 4.12 | | 5.48 | | 3.59 | | 3.27 |
| 50 | 0.1 GA + 1.2 Man + 3G | 74.09 | 16.45 | 60.64 | 16.33 | 42.16 | 12.05 | 13.97 |
| 51 | 3G | 30.29 | | 38.30 | | 21.57 | | 38.72 |
| 52 | 0.1 GA + 1.2 Man + 2.5 G | 68.98 | 4.81 | 55.32 | 52.94 | 35.58 | 5.97 | 22.55 |
| 53 | 0.1 GA + 1.2 Man + 1.5 G | 53.28 | 3.31 | 44.68 | 50.00 | 27.32 | −3.09 | 57.11 |
| 54 | 0.3 GA + 1.2 Man + 2G | 71.90 | 5.42 | 59.57 | 60.23 | 36.43 | 3.17 | 21.32 |
| 55 | 0.04 GA + 0.5 Man + 2G | 35.04 | 2.50 | 32.98 | 32.93 | 19.89 | 4.60 | 10.54 |
| 56 | 1.5 G | 18.25 | | 15.96 | | 12.14 | | 23.52 |
| 57 | 0.1 GA + 2.5 Man + 0.5G | 58.39 | −9.99 | 23.40 | −21.63 | 22.26 | −19.17 | 37.75 |
| 58 | 2.5 G | 32.48 | | 22.34 | | 17.53 | | 23.03 |
| 59 | 0.5 G | 7.97 | | 6.38 | | 3.54 | | 7.11 |
| 60 | 0.04a GA | 0.1 | | 0.1 | | 0.1 | | 0.1 |
| 61 | 0.04 aGA + 1.2Man | 20.59 | −4.85 | 9.25 | 5.35 | 14.62 | 7.90 | 12.58 |

TABLE 3-continued

| | | STUDY: HANGOVER | | | | | | |
|---|---|---|---|---|---|---|---|---|
| | | STUDY PARAMETERS | | | | | | |
| S. No. | 1 Day | MCP-1 Syn | IFN-Gamma Pro | IFN-Gamma Syn | Brain IL12 Pro | Brain IL12 Syn | Brain MCP-1 Pro | Brain MCP-1 syn |
| | Normal | | 100 | | 100.00 | | 100.00 | |
| | Alcohol | | 0 | | 0.00 | | 0.00 | |
| 1 | 0.04 GA + 1.2Xyl + 1DP | 25.30 | 18.93 | 35.31 | 22.33 | 8.25 | 34.92 | 87.64 |
| 2 | 1.2Xyl + 1 DP | | 12.74 | | 19.53 | | 17.46 | |
| 3 | 0.04 GA + 1.2Man + 1DP | 130.24 | 22 | 35.64 | 26.51 | 41.29 | 41.27 | 38.86 |
| 4 | 1.2Man + 1 DP | −80.33 | 14.97 | −25.30 | 17.67 | −22.52 | 28.57 | 14.95 |
| 5 | 0.04 GA + 2.5Man + 1DP | −16.31 | 18.51 | 11.24 | 33.02 | 26.01 | 49.21 | 36.42 |
| 6 | 2.5Man + 1 DP | −87.42 | 15.39 | −49.49 | 25.12 | −25.44 | 34.92 | 11.78 |
| 7 | 0.04aGA + 1.2Man + 1DP | 38.39 | 14.07 | −15.44 | 20.00 | −23.68 | 30.16 | −16.39 |
| 8 | 0.04 GA + 1.2Man | −87.31 | 1.32 | −85.40 | 8.84 | −33.91 | 26.98 | 20.32 |
| 9 | 0.1 GA + 1.2Man + 1DP | −45.33 | 25.12 | 11.05 | 20.47 | −21.19 | 41.27 | 41.79 |
| 10 | 0.04GA + 0.5 Ma + 0.5 DP | 143.01 | 24.07 | 206.62 | 10.18 | −6.65 | 8.51 | −18.48 |
| 11 | 0.1 GA + 1 DP | −57.48 | 13.63 | −8.09 | 14.04 | 2.54 | 14.89 | 90.21 |
| 12 | 1.2 Man | | 7.79 | | 12.28 | | 21.28 | |
| 13 | 0.1 GA | | 2.58 | | 3.16 | | 4.25 | |
| 14 | 0.15 GA + 1.2 Man + 1.0 DP | −15.24 | 24.07 | 9.46 | 28.07 | −11.12 | 44.68 | 18.76 |
| 15 | 0.15GA + 1.2 Man | | 9.74 | | 21.05 | | 34.04 | |
| 16 | 0.1 GA + 2.5 Man + 1.0 DP | −13.79 | 40.89 | 23.72 | 31.23 | −15.25 | 53.19 | 49.88 |
| 17 | 2.5 Man | | 18.22 | | 23.16 | | 27.66 | |
| 18 | 0.1GA + 1.2M + 1.25DP | −31.75 | 29.91 | 43.73 | 24.21 | 7.81 | 34.04 | −19.99 |
| 19 | 1.25 DP | | 10.44 | | 7.02 | | 17.02 | |
| 20 | 0.1 GA + 1.25 DP | 26.32 | 16.28 | 25.04 | 10.53 | 3.45 | 25.53 | 20.03 |
| 21 | 0.1 GA + 1.2 Man + 2.0 DP | −9.50 | 43.26 | 19.08 | 39.62 | −5.17 | 48.29 | −1.58 |
| 22 | 0.1 GA + 1.2 Man + 1.5 DP | −8.32 | 32.98 | 6.56 | 33.26 | −1.30 | 35.15 | −13.18 |
| 23 | 2.0 DP | | 25.96 | | 26.34 | | 23.54 | |
| 24 | 1.5 DP | | 20.58 | | 18.26 | | 14.96 | |
| 25 | 0.1 GA + 1.2 Man + 0.75 DP | −61.66 | 25.39 | 51.58 | 16.29 | −27.85 | 28.24 | −20.82 |
| 26 | 0.75 DP | | 6.38 | | 7.14 | | 10.14 | |
| 27 | 0.1 GA + 1.2 Man + 0.1 KS | −68.61 | 16.24 | 56.61 | 14.11 | −8.61 | 22.59 | −11.50 |
| 28 | 1 DP | | 12.25 | | 10.53 | | 3.58 | |
| 29 | 0.1 GA + 1.2 Man + 1 DP + 0.1 KS | −11.50 | 30.17 | 5.90 | 25.48 | 3.41 | 33.01 | 26.14 |
| 30 | 0.1 GA + 1.2 Man − 0.1 KS | 40.35 | 25.66 | 147.44 | 14.58 | −5.56 | 21.08 | −17.42 |
| 31 | 0.1 GA + 1.2 Man + 0.5 DP | −16.98 | 19.66 | 51.81 | 22.47 | 17.47 | 18.59 | −38.27 |
| 32 | 0.1 GA + 1.2 Man + 3.0 DP | −20.85 | 44.21 | 6.66 | 52.67 | 3.99 | 58.69 | −0.22 |
| 33 | 0.5 DP | | 2.58 | | 3.69 | | 4.59 | |
| 34 | 3 DP | | 31.08 | | 35.21 | | 33.29 | |
| 35 | 0.04 GA | | 1.25 | | 1.09 | | 1.15 | |
| 36 | 0.04GA + 0.5 Ma | 9.82 | 5.27 | 10.71 | 7.21 | 35.02 | 5.85 | 26.08 |
| 37 | 0.1 KS | | 0.11 | | 0.24 | | 0.19 | |
| 38 | 0.3 GA | | 7.85 | | 20.65 | | 18.92 | |
| 39 | 0.3 GA + 1.2 M + 1 DP | −16.84 | 27.61 | −1.00 | 39.13 | −9.97 | 36.94 | −15.62 |
| 40 | 0.1 GA + 1.2 M + 1 G | −30.59 | 14.57 | −53.94 | 17.39 | −25.28 | 27.93 | −17.84 |
| 41 | 0.1 GA + 1.2 M + 2 G | 31.99 | 36.96 | −8.94 | 41.30 | 17.23 | 48.95 | −0.12 |
| 42 | 2G | | 14.93 | | 20.65 | | 27.93 | |
| 43 | 1G | | 5.97 | | 8.70 | | 12.91 | |
| 44 | 0.1 GA + 1.2 M + 1 CP | −35.17 | 22.03 | −26.66 | 27.17 | 25.40 | 33.93 | −0.11 |
| 45 | 0.1 GA + 1.2 M + 2 CP | −16.07 | 52.63 | 5.41 | 44.57 | 19.14 | 54.95 | 19.45 |
| 46 | 2CP | | 24.27 | | 22.83 | | 24.92 | |
| 47 | 1CP | | 4.38 | | 7.09 | | 12.89 | |
| 48 | 1.2 Man + 1.25 DP | −50.17 | 17.91 | −1.76 | 23.91 | 23.91 | 30.93 | −19.24 |
| 49 | 0.5 Man | | 3.51 | | 4.25 | | 3.49 | |
| 50 | 0.1 GA + 1.2 Man + 3G | −74.30 | 41.52 | 47.37 | 45.95 | 12.99 | 53.49 | −7.91 |
| 51 | 3G | | 17.81 | | 25.23 | | 32.56 | |
| 52 | 0.1 GA + 1.2 Man + 2.5 G | −41.69 | 37.39 | 43.41 | 43.24 | 8.75 | 48.84 | −12.41 |
| 53 | 0.1 GA + 1.2 Man + 1.5 G | 45.81 | 29.38 | 37.69 | 27.03 | 2.96 | 32.56 | −22.12 |
| 54 | 0.3 GA + 1.2 Man + 2G | −54.78 | 41.52 | 35.83 | 43.24 | −19.30 | 53.49 | −21.48 |
| 55 | 0.04 GA + 0.5 Man + 2G | −58.16 | 23.15 | 17.56 | 27.03 | 3.98 | 32.56 | −0.03 |
| 56 | 1.5 G | | 10.97 | | 10.81 | | 16.28 | |
| 57 | 0.1 GA + 2.5 Man + 0.5G | 12.17 | 29.38 | 17.85 | 31.53 | 5.39 | 34.88 | −10.29 |
| 58 | 2.5 G | | 15.71 | | 24.32 | | 30.23 | |
| 59 | 0.5 G | | 4.13 | | 3.60 | | 6.98 | |
| 60 | 0.04a GA | | 0.1 | | 0.1 | | 0.1 | |
| 61 | 0.04 aGA + 1.2Man | 5.27 | 9.24 | 17.11 | 11.26 | −9.05 | 19.89 | −6.95 |

TABLE 4

WATER MAZE: CNS parameter: Behavioural Aspect

| Sr No | 5 day | Pro | Syn | Sr No | 5 day | Pro | Syn | Sr No | 5 day | Pro | Syn |
|---|---|---|---|---|---|---|---|---|---|---|---|
|  | Normal | 100 |  |  | Normal | 100 |  |  | Normal | 100 |  |
|  | Alcohol | 0 |  |  | Alcohol | 0 |  |  | Alcohol | 0 |  |
| 1 | 0.04 GA + 1.2Xyl + 1DP | 41.99 | 9.62 | 22 | 0.1 GA + 1.2 Man + 1.5 DP | 70.70 | 65.60 | 43 | 1G | 13.98 |  |
| 2 | 1.2Xyl + 1 DP | 36.72 |  | 23 | 2.0 DP | 50.36 |  | 44 | 0.1 GA + 1.2 M + 1 CP | 28.04 | −42.69 |
| 3 | 0.04 GA + 1.2Man + 1DP | 46.68 | 6.76 | 24 | 1.5 DP | 24.53 |  | 45 | 0.1 GA + 1.2 M + 2 CP | 55.4 | −17.03 |
| 4 | 1.2Man + 1 DP | 42.14 | 19.63 | 25 | 0.1 GA + 1.2 Man + 0.75 DP | 35.76 | 14.23 | 46 | 2CP | 29.64 |  |
| 5 | 0.04 GA + 2.5Man + 1DP | 65.24 | 20.60 | 26 | 0.75 DP | 13.15 |  | 47 | 1CP | 11.79 |  |
| 6 | 2.5Man + 1 DP | 52.51 | 9.89 | 27 | 0.1 GA + 1.2 Man + 0.1 KS | 37.74 | 107.85 | 48 | 1.2 Man + 1.25 DP | 42.66 | 83.88 |
| 7 | 0.04aGA + 1.2Man + 1DP | 44.08 | −18.51 | 28 | 1 DP | 22.38 |  | 49 | 0.5 Man | 4.95 |  |
| 8 | 0.04 GA + 1.2Man | 22.45 | 55.64 | 29 | 0.1 GA + 1.2 Man + 1 DP + 0.1 KS | 68.32 | 13.62 | 50 | 0.1 GA + 1.2 Man + 3G | 63.25 | 48.58 |
| 9 | 0.1 GA + 1.2Man + 1DP | 51.33 | 26.60 | 30 | 0.1 GA + 1.2 Man − 0.1 KS | 37.13 | 104.49 | 51 | 3G | 24.41 |  |
| 10 | 0.04GA + 0.5 Ma + 0.5 DP | 20.08 | 48.76 | 31 | 0.1 GA + 1.2 Man + 0.5 DP | 49.63 | 112.59 | 52 | 0.1 GA + 1.2 Man + 2.5 G | 59.69 | 34.50 |
| 11 | 0.1 GA + 1 DP | 19.69 | −28.93 | 32 | 0.1 GA + 1.2 Man + 3.0 DP | 67.21 | −13.09 | 53 | 0.1 GA + 1.2 Man + 1.5 G | 50.93 | 43.95 |
| 12 | 1.2 Man | 12.84 |  | 33 | 0.5 DP | 5.18 |  | 54 | 0.3 GA + 1.2 Man + 2G | 67.00 | 32.04 |
| 13 | 0.1 GA | 5.32 |  | 34 | 3 DP | 59.17 |  | 55 | 0.04 GA + 0.5 Man + 2G | 33.94 | 17.58 |
| 14 | 0.15 GA + 1.2 Man + 1.0 DP | 50.68 | −2.28 | 35 | 0.04 GA | 1.58 |  | 56 | 1.5 G | 17.22 |  |
| 15 | 0.15GA + 1.2 Man | 29.48 |  | 36 | 0.04GA + 0.5 Ma | 8.31 | 27.23 | 57 | 0.1 GA + 2.5 Man + 0.5G | 28.53 | −23.39 |
| 16 | 0.1 GA + 2.5 Man + 1.0 DP | 61.92 | 16.60 | 37 | 0.1 KS | 1.31 |  | 58 | 2.5 G | 26.22 |  |
| 17 | 2.5 Man | 25.4 |  | 38 | 0.3 GA | 15.57 |  | 59 | 0.5 G | 6.52 |  |
| 18 | 0.1GA + 1.2M + 1.25DP | 53.19 | 86.50 | 39 | 0.3 GA + 1.2 M + 1 DP | 58.28 | 14.74 | 60 | 0.04a GA | 2.1 |  |
| 19 | 1.25 DP | 10.36 |  | 40 | 0.1 GA + 1.2 M + 1 G | 28.62 | −44.01 | 61 | 0.04 aGA + 1.2Man | 14.78 |  |
| 20 | 0.1 GA + 1.25 DP | 16.36 | 4.34 | 41 | 0.1 GA + 1.2 M + 2 G | 59.39 | −0.13 |  |  |  |  |
| 21 | 0.1 GA + 1.2 Man + 2.0 DP | 72.68 | 6.07 | 42 | 2G | 22.33 |  |  |  |  |  |

After 5 alcohol doses of 4 gm/kg, per oral, mild hepatotoxicity was observed as indicated by a rise of serum ALT, AST and ALP. While formulations, having different proportions of ingredients, such as, 18-beta-Glycyrrhizin (GA), 18-alpha-glycyrrhizin (18a-GA), D-Mannitol (M), Xylitol (Xyl), L-alanine-L-glutamine (DP), Oxidized glutathione (G) and Hydrolyzed Casein protein (CP) showed mild to high degree of protection. GA as such at different concentrations (0.04-0.3%) provided low to moderate degree of protection (5-25%). As an individual ingredient, Mannitol also showed mild to moderate (10-38%) degree of protection at different doses, ranging from 0.5 to 2.5%. L-alanine-L-glutamine (DP) at the dose level of 0.5 to 1.0% showed mild effect but at higher doses (2.0 to 3.0%) high degree of protection was observed. Similarly, oxidized glutathione (G) individually showed mild to moderate degree of protection (7-38%) at 0.5 to 3.0% dose levels. Another ingredient, casein protein (CP), also showed low level of protection (10-25%) individually at 1.0 to 2.0% dose levels. In the next step, we evaluate protective activity of the combinations having two ingredients, viz., GA+M, GA+DP, M+DP, where we observed mild to moderate degree of protection with low to mild degree of synergism (0-20%). In the subsequent step, we evaluate protective activity of the combinations having three ingredients, viz., GA+M+DP, GA+M+G, GA+M+CP and we observed moderate to high degree of protection with mild to high degree of synergism (10-60 or above %). The extent of protection, however, was directly co-related with the dose of the ingredients. High degree of protection with concomitant synergism was observed in groups containing (a) 2.5% M, ≥1.0% DP, along with GA (0.04-0.1%), (b) 1.2% M, ≥2.0% G, along with GA (0.04-0.1%), (c) 1.2% M, ≥1.0% DP, along with GA (0.04-0.1%) and (d) 1.2% M, ≥1.0% CP, along with GA (0.04-0.1%). This trend was observed in most of the other parameters, such as, acetylcholine esterase activity of brain homogenate, spatial memory-learning test by Morris water maze, immunological parameters that includes pro-inflammatory cytokines and chemokines (Interleukin-12, interferon-gamma, monocyte chemoattractant protein-1, etc) and acute-phase C-reactive protein.

In single dose study the changes in liver enzymes were insignificant (data not included). But substantial changes were observed in acetylcholine esterase activity of brain homogenate, selected immunological parameters (Interleukin-12, monocyte chemoattractant protein-1, interferon-gamma, etc) and C-reactive protein. One pro-inflammatory cytokine and one pro-inflammatory chemokine have also been estimated from the brain tissue homogenate. The observed degree of protection of individual ingredients was low to moderate depending on the dose. Combinations of two ingredients, viz., GA+M, GA+DP, M+DP increased the extent of protection with low to moderate degree of synergism (0-40%). However, combinations of three ingredients, viz., GA+M+DP, GA+M+G, GA+M+CP further increased the protection from moderate to high with mild to high degree of synergism (10-60 or above %). The extent of protection, however, was directly co-related with the dose of the ingredients. High degree of protection with concomitant synergism was observed in groups containing (a) 2.5% M, ≥1.0% DP, along with GA (0.04-0.1%), (b) 1.2% M, ≥2.0% G, along with GA (0.04-0.1%), (c) 1.2% M, ≥1.0% DP, along with GA (0.04-0.1%) and (d) 1.2% M, ≥1.0% CP, along with GA (0.04-0.1%). Several studies have been conducted to pin-point the mechanism of hangover syndrome. It was observed that a significant rise in the production of cytokines IL-10, IL-12, and IFN-γ during the hangover state and could be well correlated with hangover scale scores (Kim D J, et al. (2003). Effects of alcohol hangover on cytokine production in healthy subjects. *Alcohol* 31:167-170). Thus, increase of pro-inflammatory cytokine suggested that hangovers are associated with immune functions. Present findings support the suggestion that alcohol interferes with immune functions, particularly the cytokine pathway. The formulation tested in the present study prevent the dysregulated cytokine pathway and thereby could be able to dampen the symptoms of a hangover. The most potent among the tested formulations are (a) 2.5% M, ≥1.0% DP, along with GA (0.04-0.1%), (b) 1.2% M, ≥2.0% G, along with GA (0.04-0.1%), (c) 1.2% M, ≥1.0% DP, along with GA (0.04-0.1%) and (d) 1.2% M, ≥1.0% CP, along with GA (0.04-0.1%).

It was observed that acetylcholinesterase (an enzyme that degrades acetylcholine and thereby terminates the physiological action of the neurotransmitter) activity was increased in hangover. Higher level of brain acetylcholinesterase activity, particularly in cerebral cortex and hippocampus, disrupts cognition and memory functions because it hydrolyzes Ach before it reaches the receptor (Rico E P et al, 2007, Toxicology Letters 174: 25-30; VinodTiwari et al, 2009, Behavioural Brain Research 203: 296-303). In the present study, we observed increased acetylcholinesterase activity of cerebral cortex with concomitant deficit in cognition and memory functions as reflected from Morris water maze during hangover. The formulation tested in the present study could able to prevent increased acetylcholinesterase activity and thereby able to restore the deficit in cognition and memory functions, one of the important symptoms of a hangover. The most potent among the tested formulations are (a) 2.5% M, ≥1.0% DP, along with GA (0.04-0.1%), (b) 1.2% M, ≥2.0% G, along with GA (0.04-0.1%), (c) 1.2% M, ≥1.0% DP, along with GA (0.04-0.1%) and (d) 1.2% M, ≥1.0% CP, along with GA (0.04-0.1%).

Thus, it may be concluded that above mentioned formulations, when consumed along with alcohol, may reduce hangover related symptoms compared to drinking alcohol alone.

DEFINITIONS

The following terms shall have the meanings stated therewith:
1. Active ingredient: In the present context the term active ingredient is a composite mixture derived from saponin glycoside, Amino-Acid Derivative and sugar or sugar alcohol alleviating hepatic stress, oxidative stress, modulating immunology parameters, CNS stress and Veisalgia induced by xenobiotic such as alcohol.
2. Stress: stress is a condition, which is triggered by generation of reactive oxygen species ("ROS") or reactive nitrogen species ("RNS") due to induced injury caused by xenobiotic like alcohol. This ultimately leads to imbalance and could cause hepatic stress or oxidative stress or CNS stress or all of them.
3. Amino-Acid Derivatives: a molecule consisting of one or more amino-acid molecules, such as an amino-acid monomer, dipeptide, tripeptide, oligopeptide, polypeptide, protein, or a peptide hydrolysate or a peptide residue thereof.
4. Saponin Glycoside: such as Glycyrrhizin, including a derivative or its isomer, such as 18α-Glycyrrhizin, 18β-Glycyrrhizin, 18α-mono ammonium glycyrrhizinate, 18β-mono ammonium glycyrrhizinate, or a combination thereof
5. Sugar: Compounds such as D-Maltodextrin, L-Maltodextrin, D-Maltose, L-Maltose, D-Dextrose, L-Dextrose, D-Glucose, L-Glucose, D-Trehalose, L-Trehalose, D-Sucrose, L-Sucrose, D-Lactose, L-Lactose, Hydrogenated Starch Hydrolysates, D-Fructose, D-Galactose, or mixture thereof.
6. Sugar alcohol: Compounds such as, D-Glycerol, L-Glycerol, D-Mannitol, L-Mannitol, D-erythritol, L-erythritol, D-xylitol, or L-xylitol, L-Maltitol, D-Maltitol, L-Sorbitol, D-Sorbitol, L-Lactitol, D-Lactitol, L-Isomalt, D-Isomalt or mixture thereof
7. Alcoholism: a chronic and often progressive disease that includes problems controlling drinking, being preoccupied with alcohol, continuing to use alcohol even when it causes problems, having to drink more to get the same effect (physical dependence), or having withdrawal symptoms when one rapidly decreases or stops drinking.[1]
8. Alcoholic: an individual afflicted with alcoholism.
9. Moderate drink: consumption of at least one but less than three alcoholic beverages a day for men, and at least one but less than two alcoholic beverages a day for women.
10. Binge drinking: consumption by an individual of sufficient alcohol to raise the individual's blood alcohol content above 0.08%, which, for most adults, would be reached by consuming five drinks for men, or four drinks for women, during a two-hour period.
11. Hepatoprotection: the ability to reduce stress and prevent damage to the liver
12. Veisalgia (Hangover): the medical term for a hangover, usually caused by Binge Drinking of alcohol. Symptoms often include headache, irritability, nausea, fatigue, and lethargy.
13. CNS Protection: the ability to reduce stress and prevent damage to the central nervous system, including the brain and the spinal cord.
14. Synergistic Composition: An interaction of active ingredients which, when administered simultaneously, produce an overall biological effect greater than when administered individually, i.e., having biological effects greater than the sum of individual biological effects of any of them.

The invention claimed is:
1. A beverage composition comprising:
(a) a saponin glycoside in a mass concentration range of 0.01% to 0.5%, wherein the saponin glycoside comprises Glycyrrhizin (GA), Glycyrrhizin (GA) salt, or a combination thereof, and
wherein the Glycyrrhizin (GA) comprises 18-β-Glycyrrhizin, 18-α-Glycyrrhizin, or a combination thereof;
(b) an Amino-Acid or Amino-Acid derivative in a mass concentration range of 0.04% to 3.0%, wherein Amino-Acid derivative is selected from the group consisting of a dipeptide, a tripeptide, an oligopeptide, a protein, and a protein hydrolysate; and
(c) a sugar or sugar alcohol or combination thereof in a mass concentration range of 0.5% to 3.0%, wherein the sugar is selected from the group consisting of D-Malto- dextrin, L-Maltodextrin, D-Maltose, L-Maltose, D-Dextrose, L-Dextrose, D-Glucose, L-Glucose, D-Trehalose, L-Trehalose, D-Sucrose, L-Sucrose, D-Lactose, L-Lactose, Hydrogenated Starch Hydrolysates, D-Fructose and D-Galactose, or a mixture thereof; and wherein the sugar alcohol selected from the group consisting of D-Glycerol, L-Glycerol, D-Mannitol, L-Mannitol, D-erythritol, L-erythritol, D-xylitol, or L-xylitol, L-Maltitol, D-Maltitol, L-Sorbitol, D-Sorbitol, L-Lactitol, D-Lactitol, L-Isomalt and D-Isomalt, and mixtures thereof.

2. The synergistic beverage composition as claimed in claim 1, wherein the saponin glycoside comprises Glycyrrhizin(GA) salt, which further comprises 18-α-Glycyrrhizin mono ammonium salt, 18-β-Glycyrrhizin mono ammonium salt, or a combination thereof.

3. The synergistic beverage composition as claimed in claim 1, wherein the saponin glycoside is in a mass concentration range of 0.04% to 0.5%.

4. The synergistic beverage composition as claimed in claim 1, wherein the Glycyrrhizin (GA) comprises equal parts of 18-β-Glycyrrhizin and 18-α-Glycyrrhizin.

5. The beverage composition as claimed in claim 1, wherein the Amino-Acid is an amino-acid monomer selected from the group consisting of alanine, glutamine, arginine, ornithine, arginine pryoglutamate, asparaginine, L-Aspartic acid, D-Asparatic acid, L-Carnitine, citruline, cysteine, cystine, gamma-aminobutyric acid (GABA), glutathione, glycine, histidine, L-isoleucine, L-leucine, L-lysine, methionine, phenylalanine, L-proline, pyroglutamate, serine, taurine, threonine, tyrptophan, tyrosine, L-valine, and L-Theanine.

6. The beverage composition as claimed in claim 1, wherein the Amino-Acid derivative comprises a dipeptide (DP) selected from the group consisting of L-alanyl-L-glutamine (L-Ala-L-Gln), glycyl-glycine (Gly-Gly) and L-glutamyl-L-alanine (Glu-Ala), or a combination thereof.

7. The synergistic beverage composition as claimed in claim 1, wherein the Amino-Acid or Amino-Acid derivative comprises an oligopeptide selected from the group consisting of Oxidised L-Glutathione, Reduced L-Glutathione and Glutathione.

8. The synergistic beverage composition as claimed in claim 1, wherein the Amino-Acid or Amino-Acid derivative is in a mass concentration range of 0.5% to 3.0%.

9. The synergistic beverage composition as claimed in claim 1, wherein the sugar alcohol is D-Mannitol or L-Mannitol.

10. The synergistic beverage composition as claimed in claim 1, wherein the sugar alcohol is in a mass concentration range of 0.5% to 2.5%.

11. The synergistic beverage composition as claimed in claim 1, wherein the composition further comprises pH adjusting agent and flavouring agent.

12. The synergistic beverage composition as claimed in claim 11, wherein the pH adjusting agent is selected from the group consisting of potassium sorbate (KS), monobasic sodium phosphate, dibasic sodium phosphate and tribasic sodium phosphate.

13. The synergistic beverage composition as claimed in claim 12, wherein the pH adjusting agent comprises potassium sorbate (KS) in a mass concentration range of 0.01% to 0.2%.

14. The synergistic beverage composition as claimed in claim 11, wherein the flavouring agent is selected from the group consisting of extracts of herbs, spices, fruit, and artificial flavour, in mass concentration range of 0.01% to 0.2%.

15. The synergistic beverage composition as claimed in claim 1, wherein the synergistic beverage composition comprises a composition selected from the group comprising of:

a. 18-α-Glycyrrhizin or 18-β-Glycyrrhizin, in a mass concentration of 0.04%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1%;

b. 18-α-Glycyrrhizin or 18-β-Glycyrrhizin in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1%;

c. 18-α-Glycyrrhizin or 18-β-Glycyrrhizin in a mass concentration of 0.04%, D-Xylitol, L-Xylitol, D-Mannitol or L-Mannitol in a mass concentration of 2.5%, and L-alanyl-L-glutamine (L-Ala-L-Gln) or oxidised L-glutathione in a mass concentration of 1%;

d. 18-α-Glycyrrhizin or 18-β-Glycyrrhizin in a mass concentration of 0.04%, D-Xylitol, L-Xylitol, D-Mannitol or L-Mannitol in a mass concentration of 0.5%, and L-alanyl-L-glutamine (L-Ala-L-Gln) or oxidised L-glutathione in a mass concentration of 0.5%;

e. 18-α-Glycyrrhizin or 18-β-Glycyrrhizin in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 0.5%;

f. 18-α-Glycyrrhizin or 18-β-Glycyrrhizin in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 3.0%;

g. 18-α-Glycyrrhizin or 18-β-Glycyrrhizin in a mass concentration of 0.15%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.0%;

h. 18-α-Glycyrrhizin or 18-β-Glycyrrhizin in a mass concentration of 0.3%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.0%;

i. 18-α-Glycyrrhizin or 18-β-Glycyrrhizin in a mass concentration of 0.1%, D-Xylitol, L-Xylitol, D-Mannitol or L-Mannitol in a mass concentration of 2.5%, and L-alanyl-L-glutamine (L-Ala-L-Gln) or oxidised L-glutathione in a mass concentration of 1.0%;

j. 18-α-Glycyrrhizin or 18-β-Glycyrrhizin in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.25%;

k. 18-α-Glycyrrhizin or 18-β-Glycyrrhizin in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 2.0%;

l. 18-α-Glycyrrhizin or 18-β-Glycyrrhizin in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.5%;

m. 18-α-Glycyrrhizin or 18-β-Glycyrrhizin in a mass concentration of 0.1%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.25%;

n. 18-α-Glycyrrhizin or 18-β-Glycyrrhizin in a mass concentration of 0.1%, D-Xylitol, L-Xylitol, D-Mannitol or L-Mannitol in a mass concentration of 1.2%, and casein hydrosylate protein in a mass concentration of 1.0%;

o. 18-α-Glycyrrhizin or 18-β-Glycyrrhizin in a mass concentration of 0.1%, D-Xylitol, L-Xylitol, D-Mannitol or L-Mannitol in a mass concentration of 1.2%, and casein hydrosylate protein in a mass concentration of 2.0%;

p. 18-α-Glycyrrhizin in a mass concentration of 0.05%, 18-β-Glycyrrhizin in a mass concentration of 0.05%, D-Xylitol, L-Xylitol, D-Mannitol or L-Mannitol in a mass concentration of 1.2%, and L-alanyl-L-glutamine (L-Ala-L-Gln) or oxidised L-glutathione in a mass concentration of 1.0%;

q. 18-α-Glycyrrhizin in a mass concentration of 0.05%, 18-β-Glycyrrhizin in a mass concentration of 0.05%, D-Xylitol, L-Xylitol, D-Mannitol or L-Mannitol in a mass concentration of 1.2%, and oxidised L-glutathione in a mass concentration of 1.0%;

r. equal parts 18α-Glycyrrhizin and 18-β-Glycyrrhizin in a combined mass concentration range of 0.04% to 0.1%, a sugar alcohol selected from the group consisting of D-Xylitol, L-Xylitol, D-Mannitol, and L-Xylitol in a mass concentration range of 0.5% to 2.5%, and a dipeptide comprising L-alanyl-L-glutamine (L-Ala-L-Gln) or oxidised L-glutathione in a mass concentration range of 0.5% to 3.0%; and s. saponin glycoside comprising 18α-Glycyrrhizin or 18-β-Glycyrrhizin, or a combination thereof, in a mass concentration range of 0.04% to 0.1%, a sugar alcohol selected from the group consisting of D-Xylitol, L-Xylitol, D-Mannitol, and L-Xylitol in a mass concentration range of 0.5% to 2.5%, and a dipeptide comprising L-alanyl-L-glutamine (L-Ala-L-Gln) or oxidised L-glutathione in a mass concentration range of 0.5% to 3.0%.

16. A beverage composition comprising:
(a) a saponin glycoside comprising 18-β-glycyrrhizin, 18-α-glycyrrhizin, or a combination thereof, in a mass concentration range of 0.04% to 0.5%;
(b) an amino-Acid derivative comprising a dipeptide (DP) L-alanyl-L-glutamine (L-Ala-L-Gln) and an oligopeptide oxidised L-Glutathione in a mass concentration range of 0.04% to 3.0%;
(c) a sugar alcohol comprising mannitol, xylitol or erythritol, in a mass concentration range of 0.5% to 3.0% (w/v);
(d) quantum sufficit (qs) distilled alcohol or a combination of deionized water and distilled alcohol; and
(e) optionally, a pH adjusting agent potassium sorbate (KS) in a mass concentration range of 0.01% to 0.2%, and a flavouring agent in a mass concentration range of 0.01% to 0.2%.

17. A beverage composition comprising:
(a) 18-β-Glycyrrhizin in a mass concentration range of 0.04% to 0.3%;
(b) D-mannitol in a mass concentration range of 0.5% to 2.5%; and
(c) Oxidised L-glutathione in a mass concentration range of 0.5% to 2.0%.

18. A beverage composition comprising:
(a) 18-β-Glycyrrhizin in a mass concentration range of 0.04% to 0.3%;
(b) D-mannitol in a mass concentration range of 0.5% to 2.5%; and
(c) L-alanyl-L-glutamine in a mass concentration range of 0.5% to 2.0%.

* * * * *